United States Patent
Wen et al.

(10) Patent No.: US 7,659,252 B2
(45) Date of Patent: Feb. 9, 2010

(54) TRANSDERMAL DELIVERY PEPTIDES AND METHOD OF USE THEREOF

(75) Inventors: Long-Ping Wen, Anhui (CN); Yongping Chen, Anhui (CN); Yuanyuan Shen, Anhui (CN); Xin Guo, Anhui (CN); Weiping Wang, Anhui (CN); Brian Zhang, Carlsbad, CA (US)

(73) Assignees: Novomed Technologies, Inc. (Shanghai), Shanghai (CN); University of Science & Technology of China, Anhui (CN)

( * ) Notice: Subject to any disclaimer, the term of this patent is extended or adjusted under 35 U.S.C. 154(b) by 674 days.

(21) Appl. No.: 11/531,879

(22) Filed: Sep. 14, 2006

(65) Prior Publication Data

US 2008/0305989 A1 Dec. 11, 2008

Related U.S. Application Data

(60) Provisional application No. 60/717,497, filed on Sep. 15, 2005, provisional application No. 60/740,613, filed on Nov. 29, 2005.

(51) Int. Cl.
*A61K 38/08* (2006.01)
*C07K 7/06* (2006.01)

(52) U.S. Cl. .................. 514/15; 530/327; 530/328

(58) Field of Classification Search ................. None
See application file for complete search history.

(56) References Cited

U.S. PATENT DOCUMENTS 5,534,496 A * 7/1996 Lee et al. ............... 514/17

FOREIGN PATENT DOCUMENTS

WO WO01/75067 A2 10/2001

OTHER PUBLICATIONS

Agarwal et al., 2000, "The Pilosebaceous Unit: A Pivotal Route for Topical Drug Delivery," Methods Find. Exp. Clin. Pharmacol. 22:129.
Arap et al., 1998, "Cancer Treatment by Targeted Drug Delivery to Tumor Vasculature in a Mouse Model," Science, 279:377.
BouHamdan et al., 1998, "Diversity of HIV-1 Vpr Interactions Involves Usage of the WXXF Motif of Host Cell Proteins," J. Biol. Chem. 273:8009.
Duerr et al., 2004, "Identification of Peptide Sequences that Induce the Transport of Phage Across the Gastrointestinal Mucosal Barrier," Journal of Virological Methods, 116:177-180.
Ferrer et al., 1999, "Structural and Functional Characterization of an Epitope in the Conserved C-Terminal Region of HIV-1 gp120," J. Pept. Res.: 54, 32.
Finnin et al., 1999, "Transdermal Penetration Enhancers: Applications, Limitations, and Potential," J. Pharm. Sci. 88:955.
Grams et al., 2002, "Penetration and Distribution of Three Lipophilic Probes in vitro in Human Skin Focusing on the Hair Follicle," J. Controlled Release, 83:253.
Grams et al., 2004, "Time and Depth Resolved Visualisation of the Diffusion of a Lipophilic Dye into the Hair Follicle of Fresh Unfixed Human Scalp Skin," J. Controlled Release, 98:367.
Hirvonen et al., 1996, "Transdermal Delivery of Peptides by Iontophoresis," Nat. Biotechnol. 14:1710.
Hoffman, 1997, "Topical Liposome Targeting of Dyes, Melanins, Genes, and Proteins Selectively to Hair Follicles," J. Drug Targeting, 5:67.
Joliot et al., 2004, "Transduction Peptides: From Technology to Physiology," Nature Cell Biol., 16:189.
Kalia et al., 2004, "Iontophoretic Drug Delivery," Adv. Drug Deliv. Rev. 56:619.
Kanikkannan et al., 2000, "Structure-Activity Relationship of a Chemical Penetration Enhancers in Transdermal Drug Delivery," Curr. Med. Chem. 7:593.
Kolonin et al., 2004, "Reversal of Obesity by Targeted Ablation of Adipose Tissue," Nature Med. 10:625.
Lauer et al., 1995, "Transfollicular Drug Delivery," Pharm. Res. 12:179.
Lavon et al., 2004, "Ultrasound and Transdermal Drug Delivery," Drug Discov. Today 9:679.
Li et al., 1995, "The Feasibility of Targeted Selective Gene Therapy of the Hair Follicle," Nature Med. 1:705.
Lim et al., 2003, "Penetration Enhancement in Mouse Skin and Lipolysis in Adipocytes by TAT-GKH, a New Cosmetic Ingredient," J. Cosmet. Sci., 54:483.
Lopes et al., 2005, "Comparative Study of the Skin Penetration of Protein Transduction Domains and a Conjugated Peptide," Pharm. Res. 22:750.
McAllister et al., 2003, "Microfabricated Needles for Transdermal Delivery of Macromolecules and Nanoparticles: Fabrication Methods and Transport Studies," Proc. Natl. Acad. Sci. U.S.A. 100:13755.
Meidin et al., 1998, "Low Intensity Ultrasound as a Probe to Elucidate the Relative Follicular Contribution to Total Transdermal Absorption," Pharm. Res. 15:85.
Mitragotri et al., 1995, "Ultrasound-Mediated Transdermal Protein Delivery," Science, 269:850.
Pasqualini et al., 1996, "Organ Targeting in vivo Using Phage Display Peptide Libraries," Nature, 380:364.
Prausnitz et al., 2004, "Current Status and Future Potential of Transdermal Drug Delivery," Nature, 3:115-123.

(Continued)

Primary Examiner—Anish Gupta
(74) Attorney, Agent, or Firm—Sutherland Asbill & Brennan LLP

(57) ABSTRACT

Transdermal delivery peptides for the treatment of skin diseases and/or facilitation or enhancement of transdermal delivery of pharmaceutically active agents are provided. Compositions comprising the transdermal delivery peptides and methods of therapeutic use, including the improvement of transdermal delivery of drugs or other pharmaceutically active agents, are also disclosed. Nucleic acids, expression vectors, and methods of their use, which encode the transdermal delivery peptides are disclosed. Methods are also provided for in vivo phage display for identifying further peptides with enhanced transdermal delivery capability.

15 Claims, 19 Drawing Sheets

OTHER PUBLICATIONS

Purdon et al., 2004, "Penetration Enhancement of Transdermal Delivery—Current Permutations and Limitations," Crit. Rev. Ther. Drug Carrier Syst. 21:97.

Raffii et al., 2003, "Tumor Vasculature Address Book: Identification of Stage-Specific Tumor Vessel Zip Codes by Phage Display," Cancer Cell, 4:331.

Rolland et al., 1993, "Site-Specific Drug Delivery to Pilosebaceous Structures Using Polymeric Microspheres," Pharm. Res. 10:1783.

Rothbard et al., 2000, "Conjugation of Arginine Oligomers to Cyclosporin A Facilitates Topical Delivery and Inhibition of Inflammation," Nature Med. 6:1253.

Scheuplein et al., 1971, "Permeability of the Skin," Physiol. Rev. 51:701.

Schutz-Redelmeier et al., 2004, "Antennapedia Transduction Sequence Promotes Anti Tumour Immunity to Epicutaneously Administered CTL Epitopes," Vaccine 22:1985.

Sidhu et al., 2003, "Exploring Protein—Protein Interactions with Phage Display," Chembiochem. 4:14.

Thomas et al., 2004, "The Transdermal Revolution," Drug Discov. Today 9:697.

Weiner, 1998, "Targeted Follicular Delivery of Macromolecules via Liposomes," Intl. Journal of Pharmaceutics, 162:29-38.

Whaley et al., 2000, "Selection of Peptides with Semiconductor Binding Specificity for Directed Nanocrystal Assembly," Nature, 405:665.

Williams et al., 2004, "Penetration Enhancers," Adv. Drug Deliv. Rev. 56:603.

Zaffaroni, 1991, "Overview and Evolution of Therapeutic Systems," Ann. N.Y. Acad. Sci. 618:405.

* cited by examiner

Fig. 14c

SEQUENCE LISTING

<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Ser Ser Ser Pro Ser Lys His Cys
 1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Cys Ser Ser Ser Pro Ser Lys His Cys Gly
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Cys Ser Ser Ser Pro Ser Asp His Cys Gly
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Cys Ser Ser Ser Ser Ser Lys His Cys Gly
 1               5                  10

<210> SEQ ID NO 5
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 5

Ser Ser Ser Pro Ser Lys His
  1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Cys Ser Ala Ser Pro Ser Lys His Cys Gly
  1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Cys Ser Ser Ser Ala Ser Lys His Cys Gly
  1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Cys Ser Ser Ser Pro Ala Lys His Cys Gly
  1               5                  10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Cys Ser Ser Ser Pro Ser Ala His Cys Gly
  1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Cys Ser Ser Ser Pro Ser Lys Ala Cys Gly
  1               5                  10
```

```
<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Cys Asn Ala Thr Leu Pro His Gln Cys Gly
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Pro Gly Ala Arg Pro Val Phe Pro Trp Pro Gly
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Cys(Trt)
<220> FEATURE:
<221> NAME/KEY: MOD_RES
<222> LOCATION: (3)
<223> OTHER INFORMATION: Ser(tBu)
<220> FEATURE:
<221> NAME/KEY: MOD_RES
<222> LOCATION: (4)
<223> OTHER INFORMATION: Ser(tBu)
<220> FEATURE:
<221> NAME/KEY: MOD_RES
<222> LOCATION: (5)
<223> OTHER INFORMATION: Ser(tBu)
<220> FEATURE:
<221> NAME/KEY: MOD_RES
<222> LOCATION: (7)
<223> OTHER INFORMATION: Ser(tBu)
<220> FEATURE:
<221> NAME/KEY: MOD_RES
<222> LOCATION: (8)
<223> OTHER INFORMATION: Lys(Boc)
<220> FEATURE:
<221> NAME/KEY: MOD_RES
<222> LOCATION: (9)
<223> OTHER INFORMATION: His(Trt)
<220> FEATURE:
<221> NAME/KEY: MOD_RES
<222> LOCATION: (10)
<223> OTHER INFORMATION: Cys(Trt)

<400> SEQUENCE: 13

Ala Cys Ser Ser Ser Pro Ser Lys His Cys Gly
 1               5                  10

<210> SEQ ID NO 14
<211> LENGTH: 7
<212> TYPE: PRT
<213> ORGANISM: Artificial Sequence
```

```
-continued

<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Nle
<220> FEATURE:
<221> NAME/KEY: MOD_RES
<222> LOCATION: (4)
<223> OTHER INFORMATION: D-Phe

<400> SEQUENCE: 14

Xaa Asp His Phe Arg Trp Lys
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Ser
 1
```

TRANSDERMAL DELIVERY PEPTIDES AND METHOD OF USE THEREOF

CROSS REFERENCE TO RELATED APPLICATIONS

This application claims the priority benefit of U.S. Provisional Application Ser. No. 60/717,497, filed Sep. 15, 2005, and U.S. Provisional Application Ser. No. 60/740,613, filed Nov. 30, 2005, all of which are hereby incorporated in their entirety.

FIELD OF THE INVENTION

This invention relates generally to a non-invasive percutaneous or transdermal drug delivery. In particular, this invention relates to methods of identifying peptides that enhance and/or facilitate transdermal delivery of any therapeutic agents and/or drugs, including any peptides, proteins, polynucleotides, oligonucleotides (antisense oligonucleotide agents), ribozymes, double-stranded RNA (dsRNAs), small interfering RNAs (siRNAs), RNA interferences (RNAi), gene therapy vectors, vaccines, and any conventional drugs. The invention also relates to compositions and methods which enhance the percutaneous or transdermal delivery of such therapeutic agents and drugs.

BACKGROUND OF THE INVENTION

As the largest organ of the human body, skin provides a painless and compliant interface for systemic drug delivery (Prausnitz et al., 2004, Nature Rev. Drug Discov. 3:115; Thomas and Finnin, 2004, Drug Discov. Today 9:697; and Zaffaroni, 1991, Ann. N.Y. Acad. Sci. 618:405). However, the permeability of foreign molecules, especially large hydrophilic molecules, across the skin is extremely low, primarily due to the presence of the stratum corneum, a unique hierarchical structure of lipid-rich matrix with embedded corneocytes at the outer surface of skin (Scheuplein and Blank, 1971, Physiol. Rev. 51:702).

Various chemical penetration enhancers have been studied in an attempt to open up the skin barrier but with limited success (Williams and Barry, 2004, Adv. Drug Deliv. Rev. 56:603; Purdon et al., 2004, Crit. Rev. Ther. Drug Carrier Syst. 21:97; Kanikkannan et al., 2000, Curr. Med. Chem. 7:593; and Finnin and Morgan, 1999, J. Pharm. Sci. 88:955). Without the aid of physical enhancement means such as iontophoresis (Kalia et al., 2004, Adv. Drug Deliv. Rev. 56:619; Hirvonen et al., 1996, Nat. Biotechnol. 14:1710), ultrasound (Lavon and Kost, 2004, Drug Discov. Today 9:670; Mitragotri et al., 1995, Science 269:850) or microneedles (McAllister et al., 2003, Proc. Natl. Acad. Sci. U.S.A. 100:13755; Prausnitz, 2004, Adv. Drug Deliv. Rev. 56:581), chemical penetration enhancers are generally unable to deliver therapeutic levels of large (>500 Da) hydrophilic drugs through intact skin to the systemic circulation (Bos and Meinardi, 2000, Exp. Dermatol. 9:165). Finding novel skin penetration enhancers that can overcome this limitation would significantly advance the current state of transdermal drug delivery.

In vivo phage display has been used to identify organ- and tissue-targeting peptides (Pasqualini and Ruoslahti, 1996, Nature 380:364; Arap et al., 1998, Science 279:377; Raffii et al., 2003, Cancer Cell 4:331; Kolonin et al., 2004, Nature Med. 10:625). In general, phage display describes a selection technique in which a library of variants of a peptide or protein is expressed on the outside of a phage virion, while the genetic material encoding each variant resides on the inside (Sidhu et al., 2003, Chembiochem. 4:14; Ferrer et al., 1999, J. Pept. Res.: 54, 32; BouHamdan et al., 1998, J. Biol. Chem. 273: 8009). This creates a physical linkage between each variant protein sequence and the DNA encoding it, which allows rapid partitioning based on binding affinity to a given target molecule (antibodies, enzymes, cell-surface receptors, etc.) by an in vitro selection process called panning (Whaley et al., 2000, Nature, 405, 665). In its simplest form, panning is carried out by incubating a library of phage-displayed peptides with a plate (or bead) coated with the target, washing away the unbound phage, and eluting the specifically bound phage. The eluted phage is then amplified and taken through additional binding/amplification cycles to enrich the pool in favor of binding sequences. After 3-4 rounds, individual clones are characterized by DNA sequencing and ELISA. However, the in vivo phage display method has not been used to identify peptides with transdermal capability.

Various drug molecules (Grama and Bouwstra, 2002, J. Controlled Release 83:253; Grams et al., 2004, J. Controlled Release 98:367), microspheres (Rolland et al., 1993, Pharm. Res. 10:1783) and liposome formulations (Li and Hoffman, 1995, Nature Med. 1:795; Hoffman, 1997, J. Drug Targeting 5:67) were known to exhibit follicular penetration, and hair follicles are increasing being recognized as an important route of entry for transdermal drug delivery (Lauer et al., 1995, Pharm. Res. 12:179; Agarwal et al., 2000, Methods Find. Exp. Clin. Pharmacol. 22:129). However, the definite proof for transfollicular delivery has been difficult to obtain (Meidan et al., 1998, Pharm. Res. 15:85).

A class of membrane-permeable peptides, called Protein Transduction Domains (PTDs; Joliot and Prochiantz, 2004, Nature Cell Biol. 16:189), have been reported to facilitate epicutaneous delivery of protein and peptide molecules (Rothbard et al., 2000, Nature Med. 6:1253; Schutze-Redelmeier et al., 2004, Vaccine 22:1985; Lopes et al., 2005, Pharm. Res. 22:750; Lim et al., 2003, J. Cosmet. Sci. 54:483). PTDs, however, deliver cargo only locally and not systemically, and they require physical association (usually achieved through covalent linkage) with the cargo to fulfill the delivery function.

There is an ongoing need, therefore, for developing transdermal enhancers that are highly effective in enhancing and/ or facilitating a drug to permeate the skin so that the amount of the drug in the systemic circulation or reached to the target organs, tissues, or cells is increased. In addition, using the transdermal enhancers to enhance and/or facilitate the transdermal delivery of drugs does not result in skin damage, irritation, sensitization, systemic toxicity, or the like, and can be used to effect transdermal delivery of even high molecular weight drugs such as peptides, proteins, and nucleic acids.

SUMMARY OF THE INVENTION

The present invention provides isolated transdermal delivery peptides for the treatment of skin diseases and/or facilitation or enhancement of transdermal delivery of pharmaceutically active agents. In one of the preferred embodiments, a peptide TD-1 with the amino acid sequence of ACSSSPSKHCG (SEQ ID NO:2) is provided. TD-1 comprises the sequence of a phage display peptide, TD-2 (CSSSPSKHC, SEQ ID NO:1) with the flanking A and G derived from the M13 coat protein. In another preferred embodiment, peptide analogs/variants of TD-1 are also provided. These peptide analogs/variants include TD-4 (ACSSSPSDHCG, SEQ ID NO:3) with a single amino acid substitution (K→D) from that of TD-1; TD-10 (ACSSSSSKHCG, SEQ ID NO:4) with a single point mutant (P→S) of TD-1; TD-11 (SSSPSKH, SEQ ID NO:5) that consists of only the internal 7-amino acid sequence of TD-1 and/or TD-2; TD-24 (ACSASPSKHCG, SEQ ID NO:6) with a amino acid substitution (S→A) from that of TD-1; TD-3 (ACSSSASKHCG, SEQ ID NO:7) with a single amino acid substitution (P→A) from that of TD-1; TD-6 (ACSSSPAKHCG, SEQ ID NO:8) with a single amino acid substitution (S→A) from that of TD-1; TD-22 (ACSSSPSAHCG, SEQ ID NO:9) with a single amino acid substitution (K→A) from that of TD-1; and TD-23 (ACSSSPSKACG, SEQ ID NO:10) with a single amino acid substitution (H→A) from that of TD-1.

Also provided is a chemical synthesis and use of these transdermal delivery peptides and their analogs. Certain peptides and their analogs comprising the amino acid sequences disclosed herein exhibit an ability to enhance and/or facilitate transdermal or percutaneous delivery of any pharmaceutically active agents and/or drugs, including any peptides, proteins, polynucleotides, oligonucleotides (antisense oligonucleotide agents), ribozymes, dsRNAs, RNAi, siRNAs, gene therapy vectors, vaccines, and any conventional drugs. Any techniques known to those of skill in the art for producing such peptides or proteins, including but are not limited to the expression of peptides or proteins through standard molecular biological techniques including recombinant techniques, the isolation of peptides or proteins from natural sources, or the chemical synthesis of peptides or proteins are within the scope of the present invention.

The ability of these transdermal delivery peptides and their analogs/variants to enhance and/or facilitate transdermal delivery of pharmaceutically active compounds and/or drugs is also provided. In one of the preferred embodiments, the present invention provides that TD-1 enhances and/or facilitates transdermal delivery of insulin, growth hormone, apomorphin (APO) and a peptide analogue of α-melanocyte-stimulating hormone (PT-141). The present invention further provides that these transdermal delivery peptides are capable of penetrating skin hair follicles so that they can be used for the treatment of skin diseases. In yet another preferred embodiment, the present invention provides that TD-1 provides therapeutical and/or cosmetic effects, e.g. through opening and penetrating skin hair follicles.

The present invention further provides a composition for transdermal delivery comprising a pharmaceutically acceptable carrier or vehicles and a transdermal delivery peptide that can be either chemically synthesized or produced by any conventional methods known in the art. In one of the preferred embodiments, the composition for transdermal delivery comprises a transdermal delivery peptide having an amino acid sequence as set forth in SEQ ID NO:1 (TD-2), SEQ ID NO:2 (TD-1), SEQ ID NO:4 (TD-10) or analogs thereof. In yet another preferred embodiment, the composition for transdermal delivery comprises a transdermal delivery peptide that is capable of penetrating skin hair follicles so that such composition can be used for the treatment of skin diseases. In yet another preferred embodiment, the composition for transdermal delivery further comprises a pharmaceutically active agent and/or drug so that the transdermal delivery of said pharmaceutically active agent and/or drug is facilitated or enhanced.

In yet another preferred embodiment, the pharmaceutically acceptable carriers or vehicles in the composition of the present invention comprise any acceptable materials, and/or any one or more additives known in the art. Furthermore, the composition of the present invention can also be made in any solutions and/or formulations suitable for topical and/or transdermal administration and/or any transdermal patch devices.

Also provided by the present invention are non-invasive methods for transdermal delivery. Such methods comprise the step of administering to the skin of a subject in need thereof a therapeutically effective amount of a composition for transdermal delivery comprising a pharmaceutically acceptable carrier or vehicle, and a transdermal delivery peptide. In preferred embodiments, the transdermal delivery peptides have amino acid sequences as set forth in SEQ ID NO:2 (TD-1), SEQ ID NO:1 (TD-2), or SEQ ID NO:4 (TD-10).

In yet another preferred embodiment, the present invention provides methods for enhancing transdermal delivery of pharmaceutically active agents and/or drugs comprising administering to the skin of a subject in need thereof a therapeutically effective amount of a composition for transdermal delivery comprising a pharmaceutically acceptable carrier or vehicle, a transdermal delivery peptide, and therapeutically effective amount of a pharmaceutically active agent or drug. In preferred embodiments, the transdermal delivery peptides have amino acid sequences as set forth in SEQ ID NO:2 (TD-1), SEQ ID NO:1 (TD-2), or SEQ ID NO:4 (TD-10). In yet another preferred embodiment, the pharmaceutically active agents or drugs include, but are not limited to, insulin, growth hormone, apomorphin (APO) or a peptide analogue of α-melanocyte-stimulating hormone (PT-141).

The dose ratio of the transdermal delivery peptide versus the drug to reach maximum delivery varies depending upon many patient specific factors. In certain preferred embodiments, the dose ratio of transdermal delivery peptide:drug is 1:10, 1:9.5, 1:9, 1:8.5, 1:8, 1:7.5, 1:7, 1:6.5, 1:6, 1:5.5, 1:5, 1:4.5, 1:4, 1:3.5, 1:3, 1:2.5, 1:2, 1:1.5, 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more or less. By co-administration of the transdermal delivery peptide provided by the present invention, the delivery of the desired active agents or drugs across the skin or other body surface of an animal or a human is significantly enhanced and/or facilitated, as compared to the delivery of the same active agent or drug without co-administration of the transdermal delivery peptide of the present invention. In certain embodiments of the present invention, a transdermal delivery composition comprising a mixture of at least one transdermal delivery peptide and at least one desired pharmaceutically active agent or drug in a solution, as disclosed herein, is applied to a predetermined selected skin surface of an animal.

The present invention also provides a drug delivery system for the enhanced topical or transdermal administration of a drug. Such drug delivery system comprises: (a) at least one drug reservoir containing the drug and a transdermal delivery peptide in an amount effective to enhance the amount of the drug cross the skin or body surface for a therapeutic effect without causing damage thereto; (b) a means for maintaining the system in drug and transdermal delivery peptide transmitting relationship to the skin or body surface and forming a body surface-system interface; and (c) a backing layer that serves as the outer surface of the device during use.

The transdermal delivery of a broad range of drugs may be enhanced and/or facilitated by co-administering these drugs with the transdermal delivery peptides of the present invention. Several examples are presented below. The invention provides that any drug belonging to any therapeutic class can be delivered transdermally when co-administering with the transdermal delivery peptide of the present invention.

The present invention also provides isolated nucleotides, homologs and analogs that encode peptides of TD-2 (SEQ ID NO:1), TD-1 (SEQ ID NO:2), TD-10 (SEQ ID NO:4), or portions thereof, or hybridize at highly stringent conditions to the nucleotide sequence encoding the amino acid sequence as shown in SEQ ID NO:1, SEQ ID NO:2, SEQ ID NO:4, or portions thereof, and function as transdermal delivery peptide. Moreover, the present invention provides nucleotides, homologs and analogs that comprise the nucleotide sequences encoding the amino acid sequence shown in SEQ ID NO:1, SEQ ID NO:2, SEQ ID NO:4, portions, or complements thereof.

The present invention further provides a method of screening a phage display library to identify peptides having enhanced transdermal delivery capability. The inventive method comprises the steps of: (a) applying a phage display peptide library to an area of the skin of an animal or a human being; (b) recovering phage particles from the systemic circulation and/or any organs, tissues, or cells of the animal or the human being; (c) amplifying the recovered phage for at least two rounds of in vivo selection; and (d) randomly picking and sequencing phage plaques to identify insert nucleotide sequences encoding for displayed peptides. In one of the preferred embodiments, peptides having a nucleotide sequence encoding a display peptide CSSSPSKHC (SEQ ID NO:1) (TD-2) is identified using the present invention method. This peptide shows an ability to consistently cross the skin barrier and reach the bloodstream or other tissues after transdermal administration.

BRIEF DESCRIPTION OF THE DRAWINGS

FIG. 1A shows comparison between phages carrying the TD-2 (PH-1) peptide and random phages carrying the control peptide AP-1. (n=16. ***, $P<0.001$). FIG. 1B shows inhibition of transdermal activity of phages carrying the TD-2 (PH-1) by TD-1 peptide. Phages carrying the displayed peptide TD-2 (PH-1 were topically co-applied with the various amounts of TD-1. AP-1 (AC-NATLPHQCG, SEQ ID NO:11) served as a control (n≧4).

FIG. 2A shows $^{125}$I-Insulin delivery. $^{125}$I-insulin (5,000,000 cpm) was topically co-administered to normal rats with 0 (□), 4 (■), 8 (○), 16 (▼) μg of TD-1. Radioactivity in the whole blood samples was measured at various time points after coadministration. FIGS. 2B and 2C illustrate delivery of therapeutic levels of insulin co-administered with TD-1. Porcine insulin (70 μg) was topically co-administered to streptozotocin-induced diabetic rats with 500 μg TD-1 (■), 500 μg AP-1 (□), 0.5% sodium laureth sulfate and phenyl piperazine (SLA/PP) (▲), or nothing (Δ). As additional controls, rats received 500 μg TD-1 alone topically (●) or 14 μg insulin subcutaneously (○). At various time points after administration, serum insulin concentration (FIG. 2B) and blood glucose levels (FIG. 2C) were measured. Glucose levels were normalized against the initial (0 hour) value. Mean values and the SEM are shown (n=6 for glucose and n>3 for insulin). *$P<0.05$, $P<0.01$, *$P<0.001$. FIGS. 2D and 2E shows dose-response of TD-1. Porcine insulin (70 μg) and various doses of TD-1 were topically co-administered to streptozotocin-induced diabetic rats. Serum insulin (FIG. 2D) and blood glucose (FIG. 2E) levels were measured before and 5 hours after administration. Mean values and the SEM are shown (n=6 for glucose and n≧3 for insulin). FIGS. 2F and 2G shows insulin dose response. TD-1 (500 μg) and various doses of porcine insulin were topically co-administered to streptozotocin-induced diabetic rats. Serum insulin (FIG. 2F) and blood glucose (FIG. 2G) levels were measured before and 5 hours after administration. Mean values and the SEM are shown (n=6 for glucose and n≧3 for insulin).

FIG. 10a: Delivery of different molecular forms of insulin by TD-1. 500 μg of TD-1 and 200 μg of insulin were administered to the abdominal skin of streptozotocin-induced diabetic rats in 100 μl saline (after adjusting the pH to 2.0, 3.0 and 7.0 respectively), and serum insulin was measured before and 5 hr. after administration. FIGS. 10b and 10c Time-lapse effect of TD-1. TD-1 (500 μg) in 100 μl of saline was topically administered to the abdominal skin of streptozotocin-induced diabetic rats and left for 5 minutes. The skin area was then carefully washed with an excess of saline. After various waiting periods: 0 min, 5 min, 15 min and 60 min, porcine insulin (70 μg in 100 μl saline) was then administered to the same skin site. Serum insulin level (FIG. 10b) and blood glucose level (FIG. 10c) were measured before TD-1 treatment and 5 hours after insulin administration. Co-administration (CO) of TD-1 (500 μg) and insulin (70 μg) served as the control. Mean values and the SEM are shown (n=6 for glucose and n≧3 for insulin).

(FIG. 11a-FIG. 11h) Follicular penetration of isulin-FITC facilitated by TD-1. Ten (10) μg of insulin-FITC was coadministered with 100 μg TD-1 (FIG. 11a and FIG. 11e), 100 mg AP-1 (FIG. 11b and FIG. 11f), nothing (FIG. 11c and FIG. 11g) or 0.5% SLA/PP (FIG. 11d and FIG. 11h) in 100 μl of saline solution. Microscopy of vertical (FIG. 11a-FIG. 11d) and horizontal (FIG. 11e-FIG. 11h) skin sections 2 h after administration was shown. (FIG. 11i-FIG. 11l) Time-lapse effect of TD-1 on follicular penetration of insulin-FITC. TD-1 (100 μg) was topically administered for 5 min and then carefully washed away with an excess of saline. After a waiting period of 0 (FIG. 11i), 5 (FIG. 11j), 15 (FIG. 11k) or 60 (FIG. 11l) min, insulin-FITC (10 μg) was administered to the same skin site. Microscopy of horizontal skin sections was shown. Magnification ×200. Bar=100 μm.

FIG. 13a and FIG. 13c show TD-1-FITC hair follicle penetration from vertical and horizontal skin sections, respectively, while FIG. 13b and FIG. 13d show hair follicle penetration of the control peptide SC-1-FITC from vertical and horizontal skin sections, respectively.

FIGS. 14a-14c illustrate an assessment of direct interaction between TD-1 and insulin. FIG. 14a: Binding assay using $^{125}$I-insulin, indicating that TD-1 does not bind insulin directly. $^{125}$I-insulin was added to ELISA microwell plates precoated with increasing amounts of TD-1 (left panel) or an insulin antibody (right panel), and bound radioactivity was determined after washing. FIG. 14b: Interaction between coated TD-1 and free insulin. In the left panel, insulin was added to microwells precoated with increasing amounts of TD-1, and bound insulin was detected by an anti-insulin antibody coupled with a secondary antibody conjugated with HPR. In the right panel, various amounts of insulin was coated directly on the plates and detected by the same procedure. FIG. 14c: Interaction between coated insulin and free TD-1. In the left panel, TD-1-AngII was added to wells precoated with increasing amounts of insulin, and bound TD-1-AngII was detected by an anti-AngII antibody coupled with a secondary antibody conjugated with HRP. In the right panel, various amounts of TD-1-AngII was coated directly on the plates and detected by the same procedure.

DETAILED DESCRIPTION OF THE INVENTION

Figure 1A:
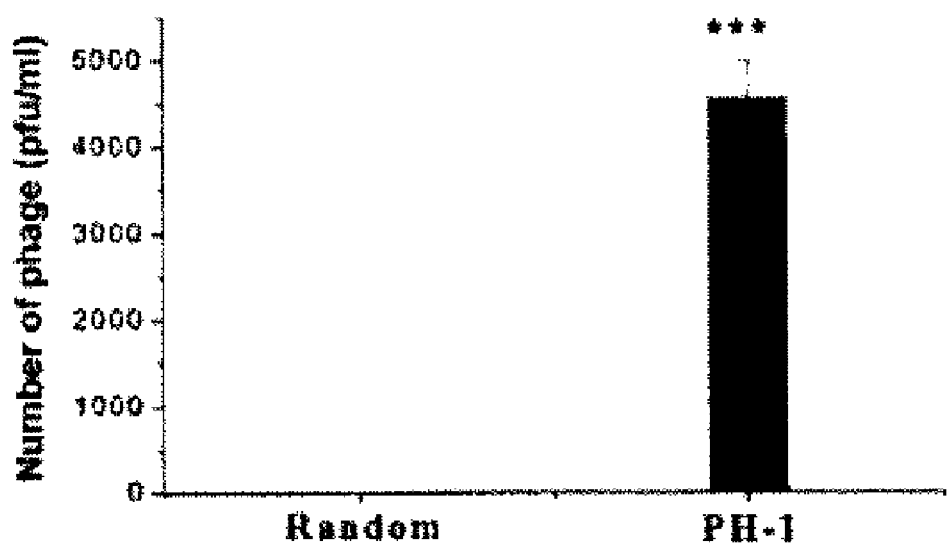
FIGS. 1A-1B illustrate transdermal activity of the phage (PH-1) and inhibition of transdermal activity of PH-1 by TD-1 peptide. Mean values for phage recovered per ml of blood and the SEM are shown.
Figure 1B:
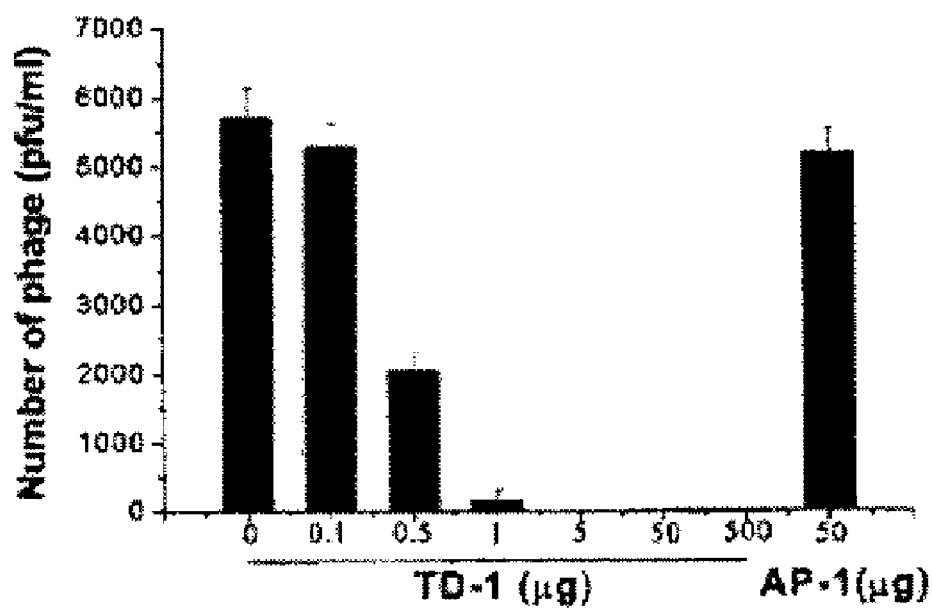

The present invention may be understood more readily by reference to the following detailed description of the preferred embodiments of the invention and the Examples included herein. However, before the present peptides, compounds, compositions, and methods are disclosed and described, it is to be understood that this invention is not limited to specific nucleic acids, specific peptides or proteins, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. It is also to be understood that as used in the specification and in the claims, "a" or "an" can mean one or more, depending upon the context in which it is used. Thus, for example, reference to "a cell" can mean that at least one cell can be utilized.

The present invention provides isolated transdermal delivery peptide and method of use these transdermal delivery peptides for the treatment of skin diseases and/or facilitating or enhancement of transdermal delivery of pharmaceutically active agents and/or drugs. In one preferred embodiment, the transdermal delivery peptides provided herein include, but are not limited to TD-1 (ACSSSPSKHCG, SEQ ID NO:2), TD-2 (CSSSPSKHC, SEQ ID NO:1), and TD-10 (AC-SSSSSKHCG, SEQ ID NO:4). The present invention further provides a composition for transdermal delivery comprising a pharmaceutically acceptable carrier or vehicle, and a transdermal delivery peptide having an amino acid sequence as set forth in SEQ ID NO:1 (TD-2), SEQ ID NO:2 (TD-1), or SEQ ID NO:4 (TD-10). In one of the preferred embodiments, the composition of the present invention further comprises a pharmaceutically active agent and/or drugs, and can be used to facilitate and/or enhance the transdermal delivery of said pharmaceutically active agent and/or drugs. In one preferred embodiment, the pharmaceutically active agents include, but are not limited to insulin, growth hormone, apomorphin, and PT-141. Isolated nucleotide sequences encode the transdermal delivery peptides provided herein are also provided.

The present invention describes a method of using in vivo selection of phage display libraries to identify displayed peptides having enhanced transdermal delivery capability. As used herein, a "phage display library" refers to a collection of phages that have been genetically engineered to express a set of peptides displayed on their outer surface. As used herein, the "displayed peptides" comprise a contiguous sequence of amino acids, and are incorporated into a protein that is displayed on the outer surface of a phage. As used herein, the term "peptide" refers to a chain of at least three amino acids joined by peptide bonds. The chain may be linear, branched, circular, or combinations thereof.

The present invention also provides compositions for enhancing transdermal therapeutic agent delivery comprising a displayed peptide and methods of treatment therewith. As used herein, the sequences of these displayed peptides generally comprise about 3 to about 100 amino acids residues, preferably, 3-20 amino acid residues, preferably, 8-12 amino acid residues. As used herein, an "amino acid residue" refers to any naturally occurring amino acid, any amino acid derivative or any amino acid mimetic known in the art. Accordingly, the displayed phage peptides encompass amino acid sequences comprising at least one of the 20 common amino acids found in naturally occurring proteins, or at least one modified or unusual amino acid known in the art or later derived.

Administration to a subject of a phage library that has been genetically engineered to express a multitude of displayed peptides of different amino acid sequences is followed by collection and identification of phage particles from the subject. As used herein, a "subject" refers to a mammal, such as a mouse, a rabbit, or a human. Phage particles often are collected from one or more organs, tissues, cell types, blood, urine, or other various body fluids. In one of the preferred embodiments, phage particles are collected from blood circulation after topical administration of the phage library onto the skin of an animal, demonstrating those phage particles containing peptides that are able to penetrate the skin of an animal and enter into systemic blood circulation.

The peptide sequences displayed on the surface of collected phage particles from the subject can be further isolated by "biopanning" (Pasqualini and Ruoslahti, 1996, Mol Psychiatry. 1(6): 423; Pasqualini, 1999, J Nucl Med. 40(5):883-8), meaning that the phage particles can be propagated in vitro between rounds of biopanning in pilus-positive bacteria. The bacteria are not lysed by the phage but rather secrete multiple copies of phage that display a particular peptide insert. Multiple rounds of biopanning can be performed. The amino acid sequence of the displayed peptide insert is determined by sequencing the DNA corresponding to that peptide insert in the phage genome. The identified peptide can then be produced as a synthetic peptide by standard protein chemistry techniques (Arap et al., 1998, Science 279(5349):377-80).

Certain phage libraries contain DNA sequences encoding peptides that are inserted in frame into a gene encoding a phage capsule protein. Others contain peptide sequences that are in part random mixtures of all twenty amino acids and in part non-random. The methods described herein for identification of peptides that have the ability to enhance transdermal drug delivery involve the in vivo administration of phage display libraries. Previously, in vivo selection studies performed in mice preferentially employed libraries of random peptides expressed as fusion proteins with the gene III capsule protein in the fUSE5 vector (Pasqualini and Ruoslahti, 1996, Mol Psychiatry. 1(6): 423). The number and diversity of individual clones present in a given library is a significant factor for the success of in vivo selection. It is preferred to use primary libraries, which are less likely to have an over-representation of defective phage clones (Koivunen et al., 1999, J Nucl Med. 140(5):883-8). Phage libraries displaying linear, cyclic, or double cyclic peptides may also be used and are within the scope of the present invention.

In a preferred embodiment, a Ph.D.™-C7C phage display peptide library is used. This library is one of the pre-made random peptide libraries that provided by New England Biolabs (Mass, Mass.). The pre-made random peptide libraries, Ph.D. libraries, have been used for myriad applications, including epitope mapping (Ph.D.™-C7C Phage Display Peptide Library Kit [online], identification of protein-protein contacts (Rozinov and Nolan, 1998, Chem. Biol. 5:713-28) and enzyme inhibitors (Rodi et al., 1999, J. Mol. Biol. 285: 197-203) and discovery of peptide ligands for GroEL (Kraft et al., 1999, J. Boil. Chem. 274:1970-85), HIV (Koolpe et al., 2002, J. Biol. Chem. 277:46974-79; Mummert et al., 2000, J. Exp. Med. 192:769-79; Hetian et al., 2002, J. Biol. Chem. 277:43137-142; White et al, 2001, Hypertension 37:449-55), semiconductor surfaces (Azzazy and Highsmith, 2002, Clin. Biochem. 35:42545) and small-molecule fluorophores (Binetruy-Tournaire et al., 2000, EMBO J. 19:1525-33) and drugs (Kragler et al., 2000, EMBO J. 19:2856-68). Bioactive receptor ligands have been identified both by panning against purified receptors (Gazouli et al., 2002, J. Pharmacol. Exp. Ther. 303:627-32; Romanczuk et al., 1999, Hum. Gene Ther. 10:2615-26; Nicklin et al., 2000, Circulation 102:231-37; Jost et al., 2001, FEBS Lett. 489:263-69) and against intact cells (Rasmussen et al., 2002, Cancer Gene Ther. 9:606-12; Tinoco et al., 2002, J. Biol. Chem. 277:36351-356; Stratmann et al., 2002, J. Clin. Microbiol. 40:4244-50; Mourez et al., 2001, Nat. Biotechnol. 19:958-61). Peptides which target specific cell types have been isolated by in vitro panning and used for cell-specific gene delivery (Rodi et al., 2002, Curr. Opin. Chem. Biol. 6:92-96; Lee et al., 2002, Arthritis Rheum. 46:2109-20; Duerr et al., 2004, J. Virol. Methods 116:177-80; Parmley et al., 1988, Gene 73:305-18). Ligands for mold spores (Berggard et al., 2002, J. Biol. Chem. 277:41954-59) and bacterial cells (Chaudhary et al., 2001, Am. J. Physiol. Cell. Physiol. 280:C1027-30) have also been identified using this system, including a peptide that specifically inhibits anthrax toxin, both in vitro and in vivo (Chen and Sigler, 1999, Cell 99:757-68). Tissue-specific peptides have been isolated by in vivo panning, in which phage is injected into a live animal, the relevant organs harvested and phage isolated from each tissue type (Biorn et al., 2004, Biochemistry 43:1928-38; Ferrer and Harrison, 1999, J. Virol. 73:5795-5802).

The randomized segment of the Ph.D.™-C7C library is flanked by a pair of cysteine residues, which are oxidized during phage assembly to a disulfide linkage, resulting in the displayed peptides being presented to the target as loops. The library has complexities in excess of 2 billion independent clones. The randomized peptide sequences in this library are expressed at the N-terminus of the minor coat protein pIII, resulting in a valency of 5 copies of the displayed peptide per virion. The first randomized position in the Ph.D.™-C7C library is preceded by Ala-Cys, and the library contains a short linker sequence (Gly-Gly-Gly-Ser) (SEQ ID NO:15) between the displayed peptide and pIII (Ph.D.™-C7C Phage Display Peptide Library Kit).

In certain embodiments, the present invention provides an identification of a peptide that has an ability to enhance transdermal delivery of any drugs and/or pharmaceutically active agents by in vivo phage display in mice. Other mammals including humans can also be used as a subject for the in vivo phage display of the present invention. In one preferred embodiment, the identification of a peptide comprises applying a phage display peptide library, for instance, the Ph.D.™-C7C phage display library, onto the abdominal skin of mice. The phage particles are then recovered from the blood circulation of mice and amplified for at least two rounds of in vivo selection. The selected phage plaques are then randomly picked up and sequenced to identify nucleotide sequences encoding for the peptide inserts that are displayed on the surface of the phage. It should be pointed out that the phage library as used herein can be applied anywhere on the skin of an animal or human being, and the transdermal phages can be recovered from any systemic circulation, any cells, tissues, or organs of the animal or human being, providing these phages have penetrated the skin barrier and reached into these areas. In one of the preferred embodiments, a displayed peptide having the amino acid sequence of CSSSPSKHC (SEQ ID NO:1) (TD-2) is provided. The phage carrying this peptide shows ability to consistently cross the skin barrier and reach bloodstream after topical administration.

The present invention also provides peptides which include peptide analogs that comprise the amino acid sequences that are identified by the in vivo phage display method. Such peptides and their included analogs exhibit an ability to enhance and/or facilitate transdermal or percutaneous delivery of any drugs, including any peptides, proteins, polynucleotides, oligonucleotides (antisense oligonucleotide agents), ribozymes, dsRNAs, RNAi, siRNAs, gene therapy vectors, vaccines, and any conventional drugs. As used herein, the term "analogs" refers to two amino acids that have the same or similar function, but that have evolved separately in unrelated organisms. As used herein, the term "analog" further refers to a structural derivative of a parent compound that often differs from it by a single element. As used herein, the term "analog" also refers to any peptide modifications known to the art, including but are not limited to changing the side chain of one or more amino acids or replacing one or more amino acid with any non-amino acids. The term "analog" also refers to an organ or structure that is similar in function to one in another kind of organism but is of dissimilar evolutionary origin.

Based on the amino acid sequences of the displayed peptides identified by in vivo phage display method, any peptides and their analogs comprising such sequences can be made by any techniques known to those of skill in the art, including but are not limited to the recombinant expression through standard molecular biological techniques, the conventional peptide/protein purification and isolation methods, and/or the synthetic chemical synthesis methods. The nucleotide and peptide sequences corresponding to various genes may be found at computerized databases known to those of ordinary skill in the art, for instance, the National Center for Biotechnology Information's Genbank and GenPept databases (National Center for Biotechnology Information). Alternatively, various commercial preparations of proteins and peptides are known to those of skill in the art.

Because the length of the identified displayed peptides of the present invention is relatively short, peptides and analogs comprising the amino acid sequences of these identified displayed peptide inserts can be chemically synthesized in solution or on a solid support in accordance with conventional techniques. Various automatic synthesizers are commercially available and can be used in accordance with known protocols. Short peptide sequences, usually from about 6 up to about 35 to 50 amino acids, can be readily synthesized by such methods. Alternatively, recombinant DNA technology may be employed wherein a nucleotide sequence which encodes a peptide and its analog of the present invention is inserted into an expression vector, transformed or transfected into an appropriate host cell, and cultivated under conditions suitable for expression.

Peptide mimetics may also be used for preparation of the peptides and their analogs of the present invention. Mimetics are peptide-containing molecules that mimic elements of protein secondary structure (Johnson et al., 1993, BIOTECHNOLOGY AND PHARMACY, Pezzuto et al., Eds., Chapman and Hall, New York). A peptide mimetic is expected to permit molecular interactions similar to the natural molecule, and may be used to engineer second generation molecules having many of the natural properties of the peptides, but with altered and even improved characteristics.

In one of the preferred embodiments, a peptide with the sequence of TD-1 (ACSSSPSKHCG, SEQ ID NO:2) is chemically synthesized based on the sequence of TD-2 with the flanking A and G derived from the M13 coat protein. In another preferred embodiment, peptide analogs of TD-1 are also synthesized. These peptides include TD-4 (ACSSSPSDHCG, SEQ ID NO:3) with a single amino acid substitution (K→D) from that of TD-1; TD-10 (ACSSSSSKHCG, SEQ ID NO:4) with a single point mutant (P→S) of TD-1; TD-11 (SSSPSKH, SEQ ID NO:5) that consists of only the internal 7-amino acid sequence of TD-1 and/or TD-2; TD-24 (ACSASPSKHCG, SEQ ID NO:6) with a amino acid substitution (S→A) from that of TD-1; TD-3 (ACSSSASKHCG, SEQ ID NO:7) with a single amino acid substitution (P→A) from that of TD-1; TD-6 (ACSSSPAKHCG, SEQ ID NO:8) with a single amino acid substitution (S→A) from that of TD-1; TD-22 (ACSSSPSAHCG, SEQ ID NO:9) with a single amino acid substitution (K→A) from that of TD-1; and TD-23 (ACSSSPSKACG, SEQ ID NO:10) with a single amino acid substitution (H→A) from that of TD-1. The ability of these peptides to enhance and/or facilitate transdermal delivery of representative drugs is also provided (See Table 2 below).

The present invention also provides chimeric or fusion peptides that comprise the amino acid sequences of the present invention, as disclosed herein. As used herein, a "chimeric or fusion peptide" comprises the amino acid sequence corresponding to TD-2 (SEQ ID NO:1), TD-1 (SEQ ID NO:2), TD-10 (SEQ ID NO:4), or analogs thereof, operatively linked, preferably at the N- or C-terminus, to all or a portion of a second peptide or protein. As used herein, "the second peptide or protein" refer to a peptide or protein having an amino acid sequence which is not substantially identical to TD-2 (SEQ ID NO:1), TD-1 (SEQ ID NO:2), TD-10 (SEQ ID NO:4), or analogs thereof, e.g., a peptide or protein that is different from TD-2 (SEQ ID NO:1), TD-1 (SEQ ID NO:2), TD-10 (SEQ ID NO:4), or analogs thereof, and is derived from the same or a different organism. With respect to the fusion peptide, the term "operatively linked" is intended to indicate that the amino acid of TD-2 (SEQ ID NO:1), TD-1 (SEQ ID NO:2), TD-10 (SEQ ID NO:4), or analogs thereof and the second peptide or protein are fused to each other so that both sequences fulfill the proposed function attributed to the sequence used.

For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In preferred embodiments, the fusion proteins of the present invention comprise the peptide and/or analog comprising amino acid sequences of the displayed peptide identified from the in vivo phage display, that is linked to a therapeutic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually any protein or peptide could be incorporated into a fusion protein comprising the peptides and analogs of the present invention. Furthermore, in certain preferred embodiments, the fusion proteins of the present invention exhibit enhanced transdermal penetration capability as compared to non-fusion proteins or peptides that have not fused with the peptides and analogs, as disclosed herein.

Methods of generating fusion peptides/proteins are well known to those of skill in the art. Such peptides/proteins can be produced, for example, by chemical attachment using bifunctional cross-linking reagents, by de novo synthesis of the complete fusion peptide/protein, or by standard recombinant DNA techniques that involve attachment of a DNA sequence encoding the peptides of present invention, as disclosed herein, to a DNA sequence encoding the second peptide or protein, followed by expression of the intact fusion peptide/protein using. For example, DNA fragments coding for the peptide sequences of TD-2 (SEQ ID NO:1), TD-1 (SEQ ID NO:2), TD-10 (SEQ ID NO:4), or analogs thereof are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al., 1992, John Wiley & Sons). Moreover, many expression vectors are commercially available that already encode a fusion moiety (e.g., a GST polypeptide). The nucleic acids encoding peptides of TD-2 (SEQ ID NO:1), TD-1 (SEQ ID NO:2), TD-10 (SEQ ID NO:4), or analogs thereof can be cloned into such an expression vector such that the fusion moiety is linked in-frame to these nucleic acids encoding peptides of TD-2 (SEQ ID NO:1), TD-1 (SEQ ID NO:2), TD-10 (SEQ ID NO:4), or analogs thereof.

In certain embodiments the peptides and analogs of the present invention may be isolated or purified. Protein purification techniques are well known in the art. These techniques involve, at one level, the homogenization and crude fractionation of the cells, tissue or organ to peptide and non-peptide fractions. The peptide/protein of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast protein liquid chromatography (FPLC) or even HPLC.

An isolated peptide is intended to refer to a peptide/protein that is purified to any degree relative to its naturally-occurring state. Therefore, an isolated or purified peptide refers to a peptide free from at least some of the environment in which it may naturally occur. Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95%, or more of the peptides in the composition.

Various methods for quantifying the degree of purification of the peptide are known in the art. These include, for example, determining the specific activity of an active fraction, or assessing the amount of peptides within a fraction by SDS/PAGE analysis. Various techniques suitable for use in peptide/protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides and their analogs always be provided in their most purified state. Indeed, it is contemplated that less substantially purified products will have utility in certain embodiments. Partial purification may be accomplished by using fewer purification steps in combination, or by utilizing different forms of the same general purification scheme. Methods exhibiting a lower degree of relative purification may have advantages in total recovery of protein product, or in maintaining the activity of an expressed protein. The invention contemplates compositions comprising the peptides and a pharmaceutically acceptable carrier.

In certain embodiments, the peptides and their analogs of the present invention may be attached to imaging agents including but are not limited to fluorescent, and/or radioisotopes including but are not limited to $^{125}$I, for imaging, diagnosis and/or therapeutic purposes. Many appropriate imaging agents and radioisotopes are known in the art, as are methods for their attachment to the peptides.

The present invention also provides isolated nucleic acids/nucleotides, homologs and analogs that comprise the nucleotide sequences encoding the peptide sequence as identified by the in vivo phage display method. As used herein, the "nucleic acids/nucleotides" may be derived from genomic DNA, complementary DNA (cDNA) or synthetic DNA. The term "nucleic acid/nucleotide" also refer to RNA or DNA that is linear or branched, single or double stranded, chemically modified, or a RNA/DNA hybrid thereof. It is contemplated that a nucleic acid within the scope of the present invention may comprise 3-100 or more nucleotide residues in length, preferably, 9-60 nucleotide residues in length, most preferably, 24-36 nucleotide residues in length. Where incorporation into an expression vector is desired, the nucleic acid may also comprise a natural intron or an intron derived from another gene. Less common bases, such as inosine, 5-methylcytosine, 6-methyladenine, hypoxanthine, and others can also be used.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding TD-2 (SEQ ID NO:1), TD-1 (SEQ ID NO:2), TD-10 (SEQ ID NO:4), or analogs thereof, as defined hereafter.

As used herein, the term "orthologs" refers to two nucleic acids from different species, but that have evolved from a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 98%, or even 99% identity, or 100% sequence identity, with all or part of the amino acid sequence of TD-2 (SEQ ID NO:1), TD-1 (SEQ ID NO:2), TD-10 (SEQ ID NO:4), or analogs thereof and will exhibit a function similar to these peptides. Preferably, the ortholog of the present invention functions as a transdermal delivery peptide. More preferably, the orthologs of the present invention have a ability to enhance or facilitate transdermal delivery of any drugs. As also used herein, the term "paralogs" refers to two nucleic acids that are related by duplication within a genome. Paralogs usually have different functions, but these functions may be related (Tatusov et al., 1997, Science 278 (5338):631-637).

As stated above, the present invention includes TD-2 (SEQ ID NO:1), TD-1 (SEQ ID NO:2), TD-10 (SEQ ID NO:4), and which are intended to include functional equivalents such as homologs and analogs thereof. To determine the percent sequence identity of two amino acid sequences (e.g., one of the sequences of SEQ ID NO:1, SEQ ID NO:2, or SEQ ID NO:4 and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:1, SEQ ID NO:2, or SEQ ID NO:4) is occupied by the same amino acid residue as the corresponding position in the other sequence (e.g., a mutant form of the sequence selected from the peptide sequences of SEQ ID NO:1, SEQ ID NO:2, or SEQ ID NO:4), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:1, SEQ ID NO:2, or SEQ ID NO:4. In other embodiments, the amino acid homologs have sequence identity over at least 5, 6, 7, 8, 9, 10, or 11 contiguous amino acid residues of the sequence disclosed herein including SEQ ID NO:1, SEQ ID NO:2, or SEQ ID NO:4.

In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences shown in SEQ ID NO:1, SEQ ID NO:2, or SEQ ID NO:4.

It is further preferred that the isolated nucleic acid homologs of the present invention encode amino acid sequences of TD-2, TD-1 or TD-10 as shown in SEQ ID NO:1, SEQ ID NO:2, or SEQ ID NO:4, respectively, or portion thereof, that is at least 90%, more preferably at least 95% identical to an amino acid sequence of SEQ ID NO:1, SEQ ID NO:2, or SEQ ID NO:4, and that functions as transdermal delivery peptides.

The determination of the percent sequence identity between two nucleic acid or peptide sequences is well known in the art. For instance, the Vector NTI 6.0 (PC) software package (InforMax, 7600 Wisconsin Ave., Bethesda, Md. 20814) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the present invention provides an isolated nucleic acid comprising a nucleotide sequence that hybridizes to the nucleotides encoding the amino acid sequences shown in SEQ ID NO:1, SEQ ID NO:2, or SEQ ID NO:4, respectively under stringent conditions. More particularly, an isolated nucleic acid molecule of the invention is at least 15 nucleotides in length and hybridizes under stringent conditions to the nucleic acid molecule comprising a nucleotide sequence encoding an amino acid sequence of SEQ ID NO:1, SEQ ID NO:2, or SEQ ID NO:4. In other embodiments, the nucleic acid is at least 15, 18, 21, 24, 30, 33, or more nucleotides in length. Preferably, an isolated nucleic acid homolog of the invention comprises a nucleotide sequence which hybridizes under highly stringent conditions to the nucleotide sequence encoding the amino acid sequence shown in SEQ ID NO:1, SEQ ID NO:2, or SEQ ID NO:4, and functions as a transdermal delivery peptide.

As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "stringent conditions" refers to hybridization in a 6×SSC solution at 65° C. In another embodiment, "highly stringent conditions" refers to hybridization overnight at 65° C. in 10× Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; Current Protocols in Molecular Biology, Chapter 2, Ausubel et al., eds., Greene Publishing and Wiley-Interscience, New York, 1995; and Tijssen, 1993, Laboratory Techniques in Biochemistry and Molecular Biology: Hybridization with Nucleic Acid Probes, Part 1, Chapter 2, Elsevier, New York, 1993.

Using the above-described methods, and others known to those of skill in the art, one of ordinary skill in the art can isolate homologs of a transdermal delivery peptide comprising amino acid sequence shown in SEQ ID NO:1, SEQ ID NO:2, or SEQ ID NO:4. One subset of these homologs are allelic variants. As used herein, the term "allelic variant"

refers to a nucleotide sequence containing polymorphisms that lead to changes in the amino acid sequences of SEQ ID NO:1, SEQ ID NO:2, or SEQ ID NO:4 without altering the functional activities. Such allelic variations can typically result in 1-5% variance in nucleic acids encoding SEQ ID NO:1, SEQ ID NO:2, or SEQ ID NO:4.

In addition, the skilled artisan will further appreciate that changes can be introduced by mutation into a nucleotide sequence that encodes the amino acid sequence of SEQ ID NO:1, SEQ ID NO:2, SEQ ID NO:4, or analogs thereof. For example, nucleotide substitutions leading to amino acid substitutions at "non-essential" amino acid residues can be made in a sequence encoding the amino acid sequence of SEQ ID NO:1, SEQ ID NO:2, SEQ ID NO:4, or analogs thereof. A "non-essential" amino acid residue is a residue that can be altered without altering the activity of said peptide, whereas an "essential" amino acid residue is required for desired activity of such peptide, such as enhance or facilitate transdermal delivery of any drugs.

Accordingly, another aspect of the invention pertains to nucleic acid molecules encoding a transdermal delivery peptide that contain changes in amino acid residues that are not essential for enhanced transdermal delivery activity. Such transdermal delivery peptides differ in amino acid sequence from a sequence contained in SEQ ID NO:1, SEQ ID NO:2, SEQ ID NO:4, or analogs thereof, yet retain enhanced transdermal delivery activities described herein. In one embodiment, the isolated nucleic acid molecule comprises a nucleotide sequence encoding peptide, wherein the peptide comprises an amino acid sequence at least about 50% identical to an amino acid sequence of SEQ ID NO:1, SEQ ID NO:2, or SEQ ID NO:4. Preferably, the peptide encoded by the nucleic acid molecule is at least about 50-60% identical to an amino acid sequence of SEQ ID NO:1, SEQ ID NO:2, or SEQ ID NO:4, more preferably at least about 60-70% identical, even more preferably at least about 70-75%, 75-80%, 80-85%, 85-90%, or 90-95% identical, and most preferably at least about 96%, 97%, 98%, or 99% identical to an amino acid sequence of SEQ ID NO:1, SEQ ID NO:2, or SEQ ID NO:4. The homologs of the transdermal delivery peptide as disclosed in the present invention preferably participate in enhancing transdermal delivery of any drugs.

An isolated nucleic acid molecule encoding a transdermal delivery peptide having sequence identity with an amino acid sequence of SEQ ID NO:1, SEQ ID NO:2, or SEQ ID NO:4 can be created by introducing one or more nucleotide substitutions, additions, or deletions into a nucleotide encoding peptide sequence of SEQ ID NO:1, SEQ ID NO:2, or SEQ ID NO:4, respectively, such that one or more amino acid substitutions, additions, or deletions are introduced into the encoded peptide and/or the side chain of the amino acids constituting the encoded peptides. Mutations can be introduced into the nucleic acid sequence encoding the peptide sequence of SEQ ID NO:1, SEQ ID NO:2, or SEQ ID NO:4 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a transdermal delivery peptide is preferably replaced with another amino acid residue from the same side chain family. Alternatively, in another embodiment, mutations can be introduced randomly along all or part of a peptide sequence for a transdermal delivery enhancer, such as by saturation mutagenesis, and the resultant mutants can be screened for an enhanced transdermal delivery activity described herein to identify mutants that retain enhanced transdermal delivery activity. Following mutagenesis of the nucleic acid sequence encoding the peptide sequence of SEQ ID NO:1, SEQ ID NO:2, or SEQ ID NO:4, the encoded peptide can be expressed recombinantly and the activity of the peptide can be determined by analyzing their transdermal delivery activity for any drugs.

The nucleotides of the present invention may be produced by any means, including genomic preparations, cDNA preparations, in vitro synthesis, RT-PCR, and in vitro or in vivo transcription. It is contemplated that peptides comprising phage displayed peptides, their variations and mutations, or fusion peptides/proteins may be encoded by any nucleic acid sequence that encodes the appropriate amino acid sequence. The design and production of nucleic acids encoding a desired amino acid sequence is well known to those of skill in the art based on standardized codons. In preferred embodiments, the codons selected for encoding each amino acid may be modified to optimize expression of the nucleic acid in the host cell of interest. Codon preferences for various species of host cell are well known in the art.

The present invention further provides a transdermal delivery composition comprising at least one pharmaceutically active agent or drug in an effective amount to provide desired pharmaceutical effects, either locally or systematically, and at least one identified transdermal delivery peptide in an amount sufficient to enhance and/or facilitate the delivery of such pharmaceutical agent or drug cross the skin or other body surface or barrier of a human or animal. As stated above, the transdermal delivery peptides provided in the composition comprise peptide sequence as identified by in vivo phage display. In one of the preferred embodiments, the transdermal delivery composition comprising a peptide having a peptide sequence of TD-2 (SEQ ID NO:1), TD-1 (SEQ ID NO:2), TD-10 (SEQ ID NO:4), or analogs thereof. In yet another preferred embodiment, the present invention provides a therapeutic and/or cosmetic composition comprising a peptide sequence of TD-2 (SEQ ID NO:1), TD-1 (SEQ ID NO:2), TD-10 (SEQ ID NO:4), or analogs thereof.

As used herein, the term "pharmacologically active agent," "therapeutic agent," "active agent," or "drug" is used interchangeably to refer to a chemical material or compound that induces a desired pharmacological, physiological effect, and include agents that are therapeutically effective, prophylactically effective, or cosmeceutically effective. The terms also encompass pharmaceutically acceptable, pharmacologically active derivatives and analogs of those active agents specifically mentioned herein, including but are not limited to, salts, esters, amides, prodrugs, active metabolites, inclusion complexes, analogs, and the like. When the terms "pharmacologically active agent," "active agent," and "drug" are used, it is to be understood that applicants intend to include the active agent per se as well as pharmaceutically acceptable, pharmacologically active salts, esters, amides, prodrugs, active metabolites, inclusion complexes, analogs, etc., which are collectively referred to herein as "pharmaceutically acceptable derivatives". The term "active agent" is also intended to encompass "cosmeceutically active agents", which are non-toxic agents that have medicinal or drug-like properties which, when applied to the surface of skin, beneficially affect the biological functioning of that skin.

The pharmaceutically active agent as used herein may be any compounds or conventional drugs that are suitable for topical or transdermal delivery and induce a desired local or systemic effects. Such substances include the broad classes of compounds/drugs normally delivered through body surfaces and membranes, including skin. While appreciating the fact that active agents may be classified in more than one category, exemplary categories of interest include: Alzheimer's drugs; analgesic agents such as narcotic analgesics; anesthetic agents; anti-acne agents; anti-anxiety drugs; anti-arthritic agents; anti-arrhythmic agents; anti-asthmatic agents and other respiratory drugs; antibiotics including antibacterial agents; anticancer agents, including antineoplastic drugs; anticholinergics and anticholinergic antagonists; anticonvulsants; antidepressants; antidiabetic agents (such as insulin); antidiarrheals; anti-emetics; antifungal agents; antiglaucoma agents; antihelminthics; antihistamines; antihyperlipidemic agents; antihypertensive agents; anti-infective agents such as antibiotics and antiviral agents; anti-inflammatory agents; antilipemic agents; antimigraine preparations; antinauseants; antineoplastic agents; antipanic agents; antiparkinsonism drugs; antipruritics; antipsoriatics; antipsychotics; antipyretics; antirheumatic agents; antispasmodics; antitubercular agents; antitussive agents; anti-ulcer agents; antiviral agents; anxiolytics; appetite stimulants and suppressants; attention deficit disorder (ADD) and attention deficit hyperactivity disorder (ADHD) drugs; benign prostatic hyperplasia agents; beta-blockers and anti-arrhythmic agents; bone density regulators; cardiovascular preparations including calcium channel blockers; central nervous system agents; central nervous system stimulants; cholesterol-lowering agents; cough and cold preparations, including decongestants; depigmenting agents; diuretics; erectile dysfunction therapies; fatty acids; gastrointestinal agents; genetic materials; hematinic agents; hemostatic drugs; herbal remedies; hormonolytics; hypnotics; hypocalcemics; hypoglycemic agents; immunosuppressive agents; leukotriene inhibitors; mitotic inhibitors; muscle relaxants; narcotic antagonists; nicotine; nutritional agents, such as vitamins, minerals, essential amino acids and fatty acids; motion sickness drugs; oxytocics; parasympatholytics; peptide drugs; prostaglandins; psychostimulants; sedatives; serotonin antagonists; serotonin receptor agonists and antagonists; steroids and other metabolic agents: such as grow hormone; sympathomimetics; thyroid preparations; tocolytics; topoimerase inhibitors; Tourette's Syndrome agents; tranquilizers; vasodilators including general coronary, peripheral and cerebral; wart preparations and combinations thereof; and sex regulation agents/drugs.

The pharmaceutically active agents as used herein may also refer to any oligonucleotides (antisense oligonucleotide agents), polynucleotides (e.g. therapeutic DNA), ribozymes, dsRNAs, siRNA, RNAi, gene therapy vectors, and/or vaccines for therapeutic use. The term "antisense oligonucleotide agent" refers to short synthetic segments of DNA or RNA, usually referred to as oligonucleotides, which are designed to be complementary to a sequence of a specific mRNA to inhibit the translation of the targeted mRNA by binding to a unique sequence segment on the mRNA. Antisense oligonucleotides are often developed and used in the antisense technology. The term "antisense technology" refers to a drug-discovery and development technique that involves design and use of synthetic oligonucleotides complementary to a target mRNA to inhibit production of specific disease-causing proteins. Virtually all diseases are associated with inadequate or over-production of proteins. Traditional small molecule drugs are designed to interact with disease-causing proteins and inhibit their function. In contrast, antisense technology permits design of drugs, called antisense oligonucleotides, which intervene at the genetic level and inhibit the production of disease-associated proteins. Antisense oligonucleotide agents are developed based on genetic information.

As an alternative to antisense oligonucleotide agents, ribozymes or double stranded RNA (dsRNA), RNA interference (RNAi), and/or small interfering RNA (siRNA), can also be used as pharmaceutically active agents for transdermal delivery. As used herein, the term "ribozyme" refers to a catalytic RNA-based enzyme with ribonuclease activity that is capable of cleaving a single-stranded nucleic acid, such as an mRNA, to which it has a complementary region. Ribozymes can be used to catalytically cleave target mRNA transcripts to thereby inhibit translation of target mRNA. The term "dsRNA," as used herein, refers to RNA hybrids comprising two strands of RNA. The dsRNAs can be linear or circular in structure. The dsRNA may comprise ribonucleotides, ribonucleotide analogs, such as 2'-O-methyl ribosyl residues, or combinations thereof. The term "RNAi" refers to RNA interference or post-transcriptional gene silencing (PTGS). The term "siRNA" refers to small dsRNA molecules (e.g., 21-23 nucleotides) that are the mediators of the RNAi effects. RNAi is induced by the introduction of long dsRNA (up to 1-2 kb) produced by in vitro transcription, and has been successfully used to reduce gene expression in variety of organisms. In mammalian cells, RNAi uses siRNA (e.g. 22 nucleotides long) to bind to the RNA-induced silencing complex (RISC), which then binds to any matching mRNA sequence to degrade target mRNA, thus, silences the gene.

As used herein, the pharmaceutically active agents also include any vectors/virus used for gene therapy. The term "gene therapy" refers to a technique for correcting defective genes responsible for disease development. Such techniques may include inserting a normal gene into a nonspecific location within the genome to replace a nonfunctional gene; swapping an abnormal gene for a normal gene through homologous recombinations, reparing an abnormal gene to resume its normal function through selective reverse mutation; and altering or regulating gene expression and/or functions of a particular gene. In most gene therapy, a normal gene is inserted into the genome to replace an abnormal or disease-causing gene. As used herein, a term "vector/virus" refers to a carrier molecule that carries and delivers the "normal" therapeutic gene to the patient's target cells. Because viruses have evolved a way of encapsulating and delivering their genes to human cells in a pathogenic manner, most common vectors for gene therapy are viruses that have been genetically altered to carry the normal human DNA. As used herein, the viruses/vectors for gene therapy include retroviruses, adenoviruses, adeno-associated viruses, and herpes simplex viruses. The term "retrovirus" refers to a class of viruses that can create double-stranded DNA copies of their RNA genomes, which can be further integrated into the chromosomes of host cells, for example, Human immunodeficiency virus (HIV) is a retrovirus. The term "adenovirus" refers to a class of viruses with double-stranded DNA genomes that cause respiratory, intestinal, and eye infections in human, for instance, the virus that cause the common cold is an adenovirus. The term "adeno-associated virus" refers to a class of small, single-stranded DNA viruses that can insert their genetic material at a specific site on chromosome 19. The term "herpes simplex viruses" refers to a class of double-stranded DNA viruses that infect a particular cell type, neurons. Herpes simplex virus type 1 is a common human pathogen that causes cold sores.

The pharmaceutically active agents as used herein also refer to vaccines that comprise a suspension of attenuated or killed microorganism (e.g. bacterial, viruses, or ricjettsiae) that are administered for the prevention, amelioration or treatment of infectious diseases. As used herein, the term "vaccine" refers to a product that produces immunity therefore protecting the body from the disease. Currently, vaccines are administered through needle injections, by mouth and by aerosol. As used herein, any vaccines currently available in the art and any vaccines in the development stage are within the scope of the present invention. Exemplary vaccines of interest include, but are not limited to flu/influenza vaccines, vaccines for hepatitis A, B, C, the measles-mumps-rubella (MMR) vaccine, the tenaus-diphtheria vaccine, the varicella (chickenpox) vaccine, the pneumococcal vaccine, and the meningococcal conjugate vaccine, and others.

The active agent administered also may be one that is cosmetically or "cosmeceutically" effective. Such agents include, for example, compounds that can reduce the appearance of aging or photodamaged skin, e.g., alpha hydroxyacids, alpha ketoacids, polymeric hydroxyacids, moisturizers, collagen, marine extract, and antioxidants such as ascorbic acid (vitamin C), $\alpha$-tocopherol (Vitamin E), $\beta$-tocopherol, $\gamma$-tocopherol, $\delta$-tocopherol, $\epsilon$-tocopherol, $\theta^1$-tocopherol, $\theta^2$-tocopherol, $\sigma$-tocopherol, and retinol (vitamin A), and/or cosmetically acceptable salts, esters, amides, or other derivatives thereof. Additional cosmetic agents include those that are capable of improving oxygen supply in skin tissue.

As used herein, the term "effective amount" or "therapeutically effective amount" of a pharmaceutically active agent is intended to mean a nontoxic but sufficient amount of a pharmaceutically active agent to provide the desired therapeutic effect. The amount that is effective will vary from subject to subject, depending on the age and general condition of the individual, the particular active agent or agents, and the like. Thus, it is not always possible to specify an exact effective amount. However, an appropriate effective amount in any individual case may be determined by one of ordinary skill in the art using routine experimentation. Furthermore, the exact effective amount of an active agent incorporated into a composition or dosage form of the present invention is not critical, so long as the concentration is within a range sufficient to permit ready application of the solution or formulation so as to deliver an amount of the active agent that is within a therapeutically effective range.

As used herein, the term "in an amount sufficient to enhance the delivery" refers to a nontoxic, non-damaging but sufficient amount of the enhancer in the composition to provide the desired increase in skin permeability and, correspondingly, the desired depth of penetration, rate of administration, and amount of drug delivered. As used herein, the term "enhance the transdermal delivery" relates to an increase in the permeability of the skin or mucosal tissue to the selected pharmacologically active agent, i.e., so that the rate and/or amount at which the agent permeates therethrough through the skin or other body surface or barrier is increased relative to the rate and/or amount that would be obtained in the absence of such transdermal delivery peptide. The enhanced delivery of the pharmaceutically active agent effected through the use of such transdermal delivery peptides can be observed by measuring the amount of diffusion of drug through animal or human skin or the desired effects of the pharmaceutically active agent as employed in the Examples herein.

As used herein, the "predetermined area" of skin or mucosal tissue refers to the area of skin or mucosal tissue through which a drug-enhancer solution and/or formulation is delivered, and is a defined area of intact unbroken living skin or mucosal tissue. That area will usually be in the range of about 5-200 $cm^2$ more usually in the range of about 5-100 $cm^2$, preferably in the range of about 20-60 $cm^2$. However, it will be appreciated by those skilled in the art of drug delivery that the area of skin or mucosal tissue through which drug is administered may vary significantly, depending on patch configuration, dose, and the like.

As used herein, the term "topical administration" is used in its conventional sense to mean delivery of a drug or pharmacologically active agent to the skin or mucosa, as in, for example, the treatment of various skin disorders. In general, topical administration provides a local effect. As used herein, the term "transdermal or percuneous delivery" is meant administration of a drug to the skin or other body surface or barrier of an individual so that the drug passes through the skin tissue or other tissues and into the individual's blood stream, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The pharmaceutically active agent may be administered, if desired, in the form of a salt, ester, amide, prodrug, derivative, or the like, provided the salt, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by March's Advanced Organic Chemistry: Reactions, Mechanisms and Structure, 5th Ed. (Wiley-Interscience, 2001). Preparation of salts, ester, amides, prodrug, etc. is known to those skilled in the art or described in the pertinent literature.

The transdermal delivery composition of the present invention can be made simply by mixing a transdermal deliver enhancer of the present invention with any pharmaceutically active agent in a solution. As used herein, solutions are homogeneous mixtures prepared by dissolving one or more chemical substances (solute) in another liquid such that the molecules of the dissolved substance are dispersed among those of the solvent. The solution may contain other pharmaceutically acceptable chemicals to buffer, stabilize or preserve the solute. Commonly used examples of solvents used in preparing solutions are saline, water, ethanol, propylene glycol or any other pharmaceutically acceptable vehicle. Preferably, the transdermal delivery peptide and the pharmaceutically active agent mixed in a solution in a dose ratio that sufficient to enhance the transdermal delivery of such active agent, providing the desired local or systemic effects. The solution containing the mixture of the transdermal delivery peptide and the active agent or drug can then be applied to a predetermined area of a human or animal skin or other body surface for a period of time sufficient to provide the desired effects.

The transdermal delivery composition of the present invention can also be made in any of formulations suitable for topical and/or transdermal administration. One embodiment of the present invention is a composition for the enhanced delivery of a drug through a body surface, comprising a formulation of: (a) a therapeutically effective amount of the drug; and (b) a transdermal delivery peptide in an amount effective to enhance the administration of the drug through the body surface without causing damage thereto. Suitable formulations of the present invention include ointments, creams, gels, lotions, pastes, patches, and the like. Ointments, as is well known in the art of pharmaceutical formulation, are semisolid preparations that are typically based on petrolatum or other petroleum derivatives. The specific ointment foundation to be used, as will be appreciated by those skilled in the art, is one that will provide for optimum drug delivery, and, preferably, will provide for other desired characteristics as well, e.g., emolliency or the like. In general, ointment foundations may be grouped in four classes: oleaginous, emulsifiable, emulsion, and water-soluble. Oleaginous ointment foundations include, for example, vegetable oils, fats obtained from animals, and semisolid hydrocarbons obtained from petroleum. Emulsifiable ointment foundations, also known as absorbent ointment foundations, contain little or no water and include, for example, hydroxystearin sulfate, anhydrous lanolin and hydrophilic petrolatum. Emulsion ointment foundations are either water-in-oil (W/O) emulsions or oil-in-water (O/W) emulsions, and include, for example, cetyl alcohol, glyceryl monostearate, lanolin and stearic acid.

Creams, as also well known in the art, are viscous liquids or semisolid emulsions, either oil-in-water or water-in-oil. Cream foundations are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also contain an alcohol and, optionally, a oil. The gelling agents are crosslinked acrylic acid polymers such as the "carbomer" family of polymers, e.g., carboxypolyalkylenes that may be obtained commercially under the Carbopol®. Also the hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin are preferred gels. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids that comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable foundation. Depending on the nature of the foundation, pastes are divided between fatty pastes or those made from single-phase, aqueous gels. The foundation in a fatty paste is generally petrolatum or hydrophilic petrolatum or the like. The pastes made from single-phase aqueous gels generally incorporate carboxymethylcellulose or the like as the foundation.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. Anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline, dioleoylphosphatidyl glycerol, dioleoylphoshatidyl ethanolamine, among others. These materials can also be mixed with N-[1-2,3-dioleyloxy)propyl]-N,N,N-triethylammonium (DOTMA) in appropriate ratios. Methods for making liposomes using these materials are well known in the art.

Micelles are known in the art and are comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used either by incorporation into the reservoir of a topical or transdermal delivery system, or into a formulation to be applied to the body surface.

Microspheres, similarly, may be incorporated into the formulations and drug delivery systems. Like liposomes and micelles, microspheres essentially encapsulate a drug or drug-containing formulation. They are generally, although not necessarily, formed from lipids, preferably charged lipids such as phospholipids. Preparation of lipidic microspheres is well known in the art and described in the pertinent texts and literature.

The transdermal delivery composition and/or therapeutic/cosmetic composition of the present invention may further comprise any one or more pharmaceutically acceptable carriers or vehicles comprising any acceptable materials, and/or any one or more additives known in the art. As used herein, the term "carriers" or "vehicle" refer to carrier materials suitable for transdermal or topical drug administration. Carriers and vehicles useful herein include any such materials known in the art, which are nontoxic and do not interact with other components of the composition in a deleterious manner.

Various additives, known to those skilled in the art, may be included in the formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

For those drugs having an unusually low rate of permeation through the skin or mucosal tissue, it may be desirable to include a second permeation enhancer in the formulation in addition to the transdermal delivery peptides disclosed herein, although in a preferred embodiment the transdermal enhancer is administered without any other permeation enhancers. Any other permeation enhancers should, like the transdermal delivery peptides of the present invention, minimize the possibility of skin damage, irritation, and systemic toxicity. Examples of classes of suitable secondary enhancers (or "co-enhancers") include, but are not limited to, fatty acids, both saturated and unsaturated; fatty alcohols; bile acids; nonionic surfactants, including esters of fatty acids, fatty (long-chain alkyl or alkenyl) esters of monohydric alcohols, diols, and polyols, diols and polyols that are both esterified with a fatty acid and substituted with a polyoxyalkylene, polyoxyalkylene fatty acid esters, polyoxyalkylene fatty ethers, polyoxyalkylene fatty ethers, and polyglyceryl fatty acid esters; amines; amides; N-alkyl-azacycloalkanones and N-alkyl-azacycloalkenones; hydrocarbon solvents; terpenes; lower alkyl esters; cyclodextrin enhancers; nitrogen-containing heterocycles; sulfoxides; and urea and its derivatives. Other specific examples of suitable co-enhancers include ethers such as diethylene glycol monoethyl ether (available commercially as Transcutolg, Gattefosse SA) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly citric acid and succinic acid. Azon®. and sulfoxides such as dimethylsulfoxide and decylmethylsulfoxide may also be used, but are less preferred.

The formulation may also contain irritation-mitigating additives to minimize or eliminate the possibility of skin irritation or skin damage resulting from the drug, the transdermal delivery peptides, or other components of the formulation. Suitable irritation-mitigating additives include, for example: .alpha.-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the formulation at a concentration effective to mitigate irritation or skin damage, typically representing not more than about 20 wt %, more typically not more than about 5 wt %, of the formulation.

The concentration of the active agent in the formulation will typically depend upon a variety of factors, including the disease or condition to be treated, the nature and activity of the active agent, the desired effect, possible adverse reactions, the ability and speed of the active agent to reach its intended target, and other factors within the particular knowledge of the patient and physician. In certain preferred embodiments, the dose ratio of transdermal delivery peptide:drug is 1:10, 1:9.5, 1:9, 1:8.5, 1:8, 1:7.5, 1:7, 1:6.5, 1:6, 1:5.5, 1:5, 1:4.5, 1:4, 1:3.5, 1:3, 1:2.5, 1:2, 1:1.5, 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1 or more or less.

An alternative and preferred method involves the use of a drug delivery system, e.g., a topical or transdermal "patch," wherein the pharmaceutically active agent and the transdermal delivery peptide is mixed and contained within a laminated structure that is to be affixed to the skin. In such a structure, the drug composition is contained in a layer, or "reservoir," underlying an upper backing layer that serves as the outer surface of the device during use. The laminated structure may contain a single reservoir, or it may contain multiple reservoirs.

Accordingly, another embodiment of the present invention is a system for the enhanced topical or transdermal administration of a drug, comprising: (a) at least one drug reservoir containing the drug and a transdermal delivery peptide in an amount effective to enhance the amount of the drug cross the skin or body surface without causing damage thereto; (b) a means for maintaining the system in drug and transdermal delivery peptide transmitting relationship to the skin or body surface and forming a body surface-system interface; and (c) a backing layer that serves as the outer surface of the device during use.

In one embodiment, the drug reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the pharmaceutically active agent, the transdermal delivery peptide of the present invention, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing the drug, the transdermal delivery peptide of the present invention, or other components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure preferably includes a release liner. Immediately prior to use, this layer is removed from the device so that the system may be affixed to the skin. The release liner should be made from a drug/vehicle impermeable material, and is a disposable element, which serves only to protect the device prior to application. Typically, the release liner is formed from a material impermeable to the pharmacologically active agent and the transdermal delivery peptide of the present invention, and is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or pouch, or it may be a hydrogel reservoir, or may take some other form. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly(hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a transdermal delivery peptide of the present invention, an additional enhancer, or some other component contained in the drug delivery system.

A rate-controlling membrane, if present, will be included in the system on the skin side of one or more of the drug reservoirs. The material used to form such a membrane is selected so as to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5-200 $cm^2$, preferably 5-100 $cm^2$, more preferably 20-60 $cm^2$. That area will vary, of course, with the amount of drug to be delivered and the amount of the drug cross through the body surface. Larger patches can be used to accommodate larger quantities of drug, while smaller patches can be used for smaller quantities of drug and/or drugs that exhibit a relatively high permeation rate.

Such drug delivery systems may be fabricated using conventional coating and laminating techniques known in the art. For example, adhesive matrix systems can be prepared by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by soaking in a drug/vehicle mixture. In one preferred embodiment, transdermal systems of the present invention are fabricated by solvent evaporation, film casting, melt extrusion, thin film lamination, die cutting, or the like. The transdermal delivery peptide will generally be incorporated into the device during patch manufacture rather than subsequent to preparation of the device.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating an adhesive overlayer, the delivery system will remain in place for the required period of time.

Other types and configurations of transdermal drug delivery systems including electrophoresis and/or iontophoresis, may also be used in conjunction with the method of the present invention, as will be appreciated by those skilled in the art of transdermal drug delivery.

As with the topically applied formulations of the present invention, the drug and the transdermal delivery peptide composition contained within the drug reservoir(s) of these laminated systems may comprise a number of additional components. In some cases, the drug and the transdermal delivery peptide may be delivered neat, i.e., in the absence of additional liquid. In other cases, the drug and the transdermal delivery peptide will be dissolved, dispersed or suspended in a suitable pharmaceutically acceptable vehicle, typically a saline solution, solvent or gel. Other components that may be present include preservatives, stabilizers, surfactants, solubilizers, additional enhancers, and the like.

The present invention provides non-invasive methods for enhancing and/or facilitating a transdermal or percutaneous delivery of any desired pharmaceutically active agents and/or drugs. In one of the preferred embodiments, the invention method comprises the step of co-administering to a selected skin surface, at least one desired pharmaceutically active agent or drug in a pharmaceutical effective amount for the treatment of a disease, and at least one transdermal delivery peptide identified by in vivo phage display method in an effective amount to enhance the amount of the pharmaceutical active agent or drug through the skin or other body surface and enter into the systemic circulation. As used herein, the term "treatment" refers to reduction in severity and/or frequency of symptoms, elimination of symptoms and/or underlying cause, prevention of the occurrence of symptoms and/or their underlying cause, and improvement or remediation of damage. The term "treatment" also encompasses both prevention of a disorder in a predisposed individual and treatment of the disorder in a clinically symptomatic individual.

While the method of delivery of the pharmaceutically active agent may vary, the method will typically involve application of a solution, a formulation or drug delivery system containing a transdermal delivery peptides of the present invention and a pharmaceutically active agent or drug to a predetermined area of the skin or other body surface for a period of time sufficient to provide the desired local or systemic effect. The method may involve direct application of the composition as a solution, an ointment, gel, cream, or the like, or may involve use of a drug delivery device.

The amount of active agent administered will depend on a number of factors and will vary from subject to subject and depend on the particular drug administered, the particular disorder or condition being treated, the severity of the symptoms, the subject's age, weight and general condition, and the judgment of the prescribing physician. Other factors, specific to transdermal drug delivery, include the solubility and permeability of the carrier and adhesive layer in a drug delivery device, if one is used, and the period of time for which such a system will be fixed to the skin or other body surface. The minimum amount of drug is determined by the requirement that sufficient quantities of drug must be present in a device or composition to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

Accordingly, the present invention provides a novel and highly effective methods for increasing the amount of a pharmaceutically active agent or drug across the body surface (skin or mucosal tissue) of a human or animal. The transdermal delivery peptides disclosed herein, employed in specific amounts relative to a formulation or drug reservoir, may be used as permeation enhancers with a wide variety of drugs and drug types, including free acids, free bases, acid addition salts of basic drugs, basic addition salts of acidic drugs, non-ionizable drugs, peptides and proteins. Several examples are presented below. Practically, any drug belonging to any therapeutic class can be delivered transdermally when co-administering with the transdermal delivery peptides of the present invention. Surprisingly, the increase in permeation is not accompanied by any noticeable tissue damage, irritation, or sensitization. The invention thus represents an important advance in the field of drug delivery.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

In Vivo Phage Display to Identify Peptides with Transdermal Enhancing Capability Phage library screening: One of the three pre-made random peptide libraries, a disulfide-constrained heptapeptide (Ph.D.™-C7C) library provided by New England Biolabs (Mass, Mass.), was used to identify peptides with transdermal enhancing capability. The randomized segments in this library are flanked by a pair of cysteine residues, which are oxidized during phage assembly to a disulfide linkage, resulting in the displayed peptides being presented to the target as loops (Ph.D.™-C7C Phage Display Peptide Library Kit). The library has complexities in excess of 2 billion independent clones. The randomized peptide sequences in this library are expressed at the N-terminus of the minor coat protein pIII, resulting in a valency of 5 copies of the displayed peptide per virion. The first randomized position in the Ph.D.-C7C library is preceded by Ala-Cys. The library contains a short linker sequence (Gly-Gly-Gly-Ser) (SEQ ID NO:15) between the displayed peptide and pIII (Ph.D.™-C7C Phage Display Peptide Library Kit).

Balb/c nude mice (Slaccas, Shanghai, China) were maintained in gnotobiotic isolators. Mice were anethetized using Vrethane (Midwest Group, Beijing, China). $10^{12}$ plague forming units (pfu) of Ph.D.-C7C phage library (New England Biolabs, Mass.) in 100 µl of saline was applied onto the abdominal skin of nude mice and spread evenly over an area of approximately 3.0 cm×3.0 cm using the side of a pipet tip. The phage particles were recovered from the blood circulation and further amplified and used for the next round of in vivo selection. That is, one hour after the phage administration 1 ml of blood was withdrawn from the heart and mixed with 0.5 ml of rapidly-growing *E. Coli* ER 2738. After 30 min of incubation, the recovered phage were amplified in 20 ml of LB medium for 6 hr. Amplified phage were re-suspended in PBS and used for the second round of screening, following the same procedure. Approximately 150 phages were recovered from the first round, and the amplified phage from the first round exhibited a transdermal efficiency two orders of magnitude higher than the library phage (see Table 1).

TABLE 1

| Transdermal Activity of 1st Round Recovered Phage and Library Phage | | |
|---|---|---|
| | C7C Library (# of phage/ml blood) | 1st Round Recovered Phage (# of phage/ml blood) |
| Exp. 1 | 160 | 18500 |
| Exp. 2 | 90 | 12700 |

Phages recovered from the blood sample of the second round were plated out on LB plates containing X-gal (5-bromo-4-chloro-3-indolyl-β-D-galactoside) and IPTG (isopropyl-β-D-thiogalactoside). After the second round, twelve blue plagues were randomly picked and subject to DNA sequencing with DNA Automatic Sequencer (ABI3730). Eight of them contained identical insert nucleotide sequence, which coded for a displayed peptide TD -2 (or PH-1) (CSSSPSKHC, SEQ ID NO:1).

Example 2

Chemical Synthesis of Transdermal Delivery Peptides and their Analogues

Peptide synthesis: All peptides were synthesized by Shanghai GL Biochemicals, using standard solid-phase FMOC method with automatic peptide synthesizer (CS536-1381, CS Bio Co., Menlo Park, Calif.) and purified to >95% by high-performance liquid chromatography (HPLC). The identities of the peptides were independently verified using a mass spectrometer (BIFLEX™ III, Bruker, Germany).

Specifically, a peptide with the sequence TD-1 (AC-SSSPSKHCG, SEQ ID NO:2) was synthesized. The flanking A and G were derived from the M13 coat protein. The TD-1 peptide synthesis was performed using standard Fmoc methodology manually or on an automated synthesizer (Advanced ChemTech). A typical manual synthesis protocol is as the following: approximately 0.2 mmol Fmoc-Gly-Wang resin was added to a manual reaction vessel (Peptides International) and allowed to swell for 2 hrs in DMF. De-protection of the Fmoc group was performed with 20% piperidine in DMF for 2 mins, followed by another 20-mins 20% piperidine treatment. A positive Kaiser test resulted, indicating free amine groups on the resin. The amino acids residues were added to the amide resin in a cycle fashion as follows: addition of 3-fold excess of the Fmoc-amino acid specified by the TD-1 sequence, 3-fold excess of 1-hydroxybenzotriazole (HOBT) and 3.1-fold excess of 1,3-diisopropylcarbodiimide in DMF.

The coupling reaction is done by bubbling with nitrogen gas for 2 hrs, followed by emptying of the reaction vessel under vacuum. The resin-$N^\alpha$-protected peptideis were washed with DMF (5×1 min) to remove excess reagents, followed by $N^\alpha$-Fmoc deprotection with 20% piperidine in DMF as described above. The reaction vessel is washed with DMF to remove the piperidine, and cycle repeated for the next amino acid on the sequence. Upon complete synthesis of the side chain protected $N^\alpha$-Fmoc-Ala-Cys(Trt)-Ser(tBu)-Ser(tBu)-Ser(tBu)-Pro-Ser(tBu)-Lys(Boc)-His(Trt)-Cys(Trt)-Gly-resin (SEQ ID NO:13) conjugate, the peptide-resin was washed with DMF (4×1 min) and dried in vacuum. $N^\alpha$-Fmoc group was removed by 20% piperidine in DMF. The side chain de-protection and peptide-resin cleavage were achieved by incubation in 10 ml of cleavage cocktail (95% trifluoroacetic acid, 2.5% water, 2.5% triisopropylsilane) for 3 hrs at 500 rpm. The reaction products were transferred to pre-weighed 50 ml conical tubes and precipitated with cold anhydrous ethyl ether (up to 50 ml). The crude peptide was dried in vacuum for 48 hrs. A 70- to 100 mg sample of crude peptide was purified by reverse phase high performance liquid chromatography (RP-HPLC) using a Shimadzu chromatography system with a photodiode array detector and a semi-preparative RP-HPLC C18 bonded silica column and lyophilized. The purity of the peptides was assessed by analytical RP-HPLC and its molecular weight was assessed by MS.

Control peptides AP-1 with the sequence ACNATLPHQCG (SEQ ID NO:11) and SC-1 with the sequence HPGARPVFPWPG (SEQ ID NO:12) were also synthesized using the same method. The AP-1 peptide is a cyclic 11-mer with the same flanking amino acids but containing an unrelated internal sequence. These peptides were synthesized by the same Fmoc method as described above. FITC was linked to the N-terminus of TD-1 and SC -1 through an aminocaproic (Acp) spacer.

Example 3

Inhibiting Transdermal Activity of Phages Carrying the Display Peptide TD-2 (PH-1) by TD-1

Phage delivery: Male Wistar rats (180 g to 220 g) were housed at a constant temperature (22° C.) and relative humidity (60%) with a fixed 12 hr. light/dark cycle, and free access to food and water. While the animals were anesthetized with Vrethane (5 ml/kg of 20% solution), the hair in an area of approximately 3.0 cm×3.0 cm on the abdomen was carefully trimmed using scissors, with caution not to damage the skin (rats with any visible sign of skin damage were not used). $10^{12}$ pfu of phage (PH-1) carrying the display peptide TD-2 (SEQ ID NO:1) or control phage randomly picked from the library that carries a displayed peptide with the sequence AP-1 (SEQ ID NO:11) were applied to the center of the area and spread evenly over the entire area using the side of a pipet tip. One hour after the phage administration blood was withdrawn from the tail vein and immediately assayed for phage titre according to manufacturer's protocol.

When tested in Wistar rats, a representative phage carrying the TD-2 (PH-1) peptide showed consistently crossing the skin barrier and reaching bloodstream, achieving an average titre of 4556 infective phage particles per milliliter of blood at 1 hour post topical administration (FIG. 1A). In contrast, the control peptide AP-1 exhibited a transdermal activity of less than 0.2% of that for the phage PH-1, with no infective phage particles detected in the bloodstream (FIG. 1A).

When co-administered TD-1 with phages that carry the TD-2 peptide (PH-1), TD-1 inhibited the transdermal activity of phages carrying the TD-2 peptide (PH-1 in a dose-dependent manner. At amounts of over 5 μg, TD-1 completely abolished the transdermal activity of phages carrying the TD-2 peptide (PH-1), while the control peptide AP-1 showed no effect on the ability of phages that carry the TD-2 peptide (PH-1) to traverse the skin (FIG. 1B), suggesting that the transdermal activity of phages that carry the TD-2 peptide (PH-1 involves a specific interaction between the displayed peptide of TD-2 and some component of the skin.

In contrast to the effect on phages carrying the TD-2 displayed peptide (PH-1, TD-1 enhanced the transdermal penetration of a control phage, but the activity was relatively low and inconsistent as this enhancing activity was observed on only 20% of the tested rats. (Chen et al., unpublished, data not shown).

Example 4

Enhancing Transdermal Delivery of Insulin by TD-1

$^{125}$I-insulin delivery: $^{125}$I-insulin (specific activity: 170 μCi/μg) was prepared at Beijing Atom HighTech, (Beijing, China) using Bolton-Hunter procedure (Bolton & Hunter, 1973, Biochem. J. 133:529), and was purified by HPLC. Five Million cpm of $^{125}$ I-insulin in 100 μl of saline was co-administered with three different doses of TD-1 or with 16 μg of AP-1 to the exposed abdominal skin of anesthetized Wistar rats. Blood was withdrawn from the tail vein at the various time points and assayed for $^{125}$I radioactivity in the systemic circulation with Gamma Radioimmunoassay Counter (GC-911, USTC Chuangxin Co., Hefei, China).

Insulin delivery: In particular, male Wistar rats were given intraperitoneal injection of straptozotocin (60 mg/kg; Sigma-Aldrich, St. Louis, Mich.) to make these rats in diabetic states. Seven to 10 days post injection blood glucose level was measured using One-Touch Ultra Glucometer (LifeScan, Milpitas, Calif.). The straptozocin-induced (SD-induced) diabetic rats with blood glucose level of over 20 mmol/l (normal rats are between 4 and 6 mmol/l) were selected and randomly assigned to different treatment groups, with 6 rats for each group. To assess the ability of TD-1 to deliver insulin transdermally, $^{125}$I-insulin was co-administered topically with three different doses of TD-1 to the rat abdominal skin exposed after hair trimming and the radioactivity of $^{125}$I in the systemic circulation was measured. To test whether TD-1 can deliver therapeutic levels of insulin, 70 μg of pharmaceutical-grade (>98%, 30 IU/mg) porcine insulin (Xuzhou Pharmaceuticals, Xuzhou, China) and 500 μg of TD-1 in 100 μl saline (the ratio of porcin insulin:TD-1 was 7:50 (about 1:7.5)) were topically co-administered to the rat exposed abdominal skin. In comparison, each rat in the chemical enhancer group was topically administered 100 μl of 1:1 PBS:ethanol solution containing 70 μg insulin, 0.35% (wt/vol) sodium laureth sulfate (SLA; Sigma) and 0.15% (wt/vol) phenyl piperazine (PP; Sigma). The SLA/PP is a chemical enhancer combination recently identified from high-throughput screening (Karande et al., 1994, Nature Biotech. 22:192). Moreover, in other transdermal treatment groups, 100 μl saline was given to each rat in that group. For the subcutaneous treatment group, 14 μg of insulin per rat was injected.

Dose dependent studies were also conducted at various time points, such as 0, 2, 5, 8 and 11 hours after topical administration, and 0, 1, 2, 3 and 5 hours after subcutaneous injection. Blood was drawn from the rat tail vein at these time points and assayed for blood glucose as described above and serum insulin by radioimmunoassay (Immunotech, Czech). For these studies, the indicated amounts of insulin and TD-1 peptide were topically administered, with blood glucose and serum insulin levels measured before and 5 hours after administration, as described above.

Figure 2A:
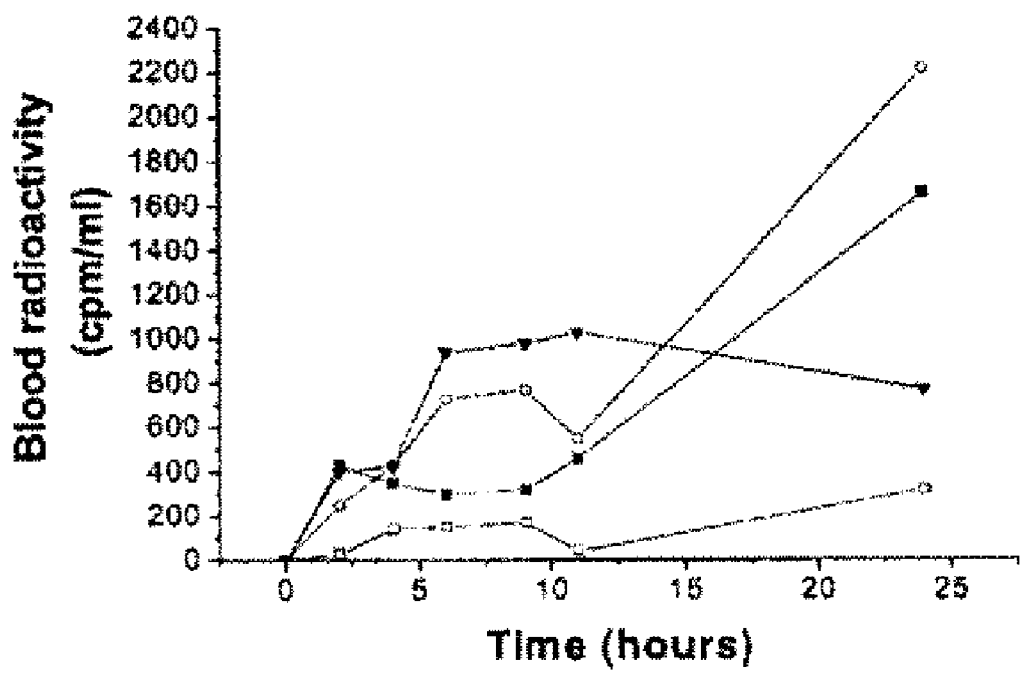
FIGS. 2A-2G illustrate systemic protein drug (insulin) delivery in rats mediated by TD-1.

Those studies showed that, in the absence of TD-1, i.e., TD-1 at 0 μg (symbol □ in FIG. 2A), $^{125}$I-insulin was unable to reach the bloodstream. However, when topically co-administration of $^{125}$I-insulin with either 4 μg, 8 μg, or 16 μg of TD-1 to the rat abdominal skin exposed after hair trimming, significant level of $^{125}$I in the whole blood was detectable in 2 hours after the co-administration and continued to increase for the whole duration, i.e., 24 hours, of the experiment (symbols ■, ○, and ▼ in FIG. 2A), indicating that TD-1 has a capability to deliver insulin transdermally. These studies indicated that all three doses of TD -1 were effective.

In addition, topically co-administered TD-1 and porcine insulin at 500 μg/70 μg ratio in the saline solution to straptozocin-induced diabetic rats indicated that TD-1 can deliver insulin transdermally at the therapeutic levels. In these studies, elevated serum insulin level was detectable 2 hours after the co-administration, and was peaked at 5 hours after the co-administration, and then returned to basal level at 11 hours (symbol □ in FIG. 2B). Correspondingly, a decrease of blood glucose level was seen 2 hours after the co-administration, with the lowest blood glucose level (<25% of the initial blood glucose level) reached at 8 hours after the co-administration, and the significantly reduced level sustained for at least II hours (symbol ■ in FIG. 2C). In contrast, the controlled phage peptide, AP-1 was ineffective in elevating serum insulin and lowering blood glucose levels (symbol □ in FIGS. 2B and 2C). The mixture of the chemical enhancer combination, sodium laureth sulfate and phenyl piperazine (SLA/PP), also showed no effect in elevating serum insulin and lowering blood glucose levels (symbol ▲ in FIGS. 2B and 2C).

Figure 2B:
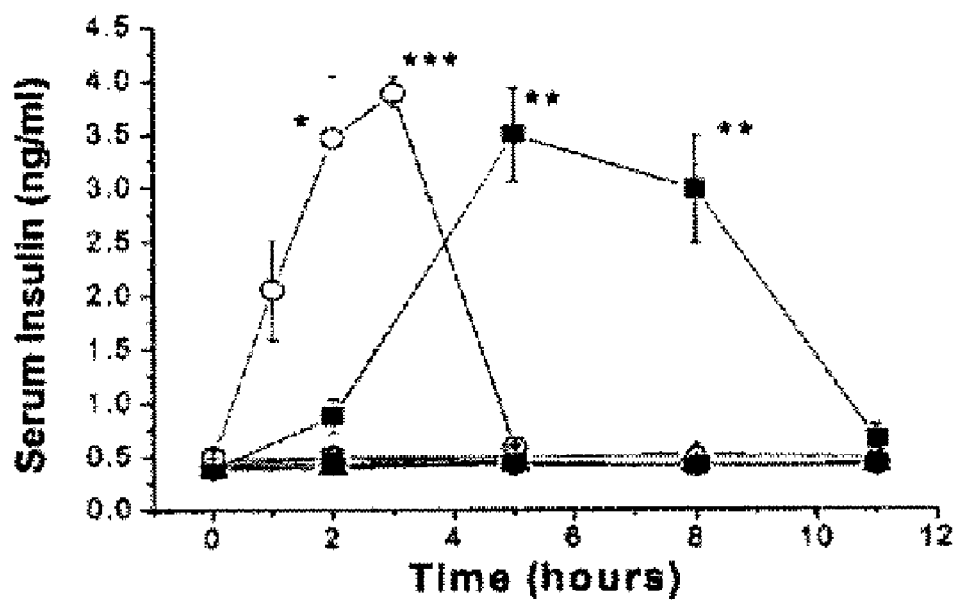
Figure 2C:
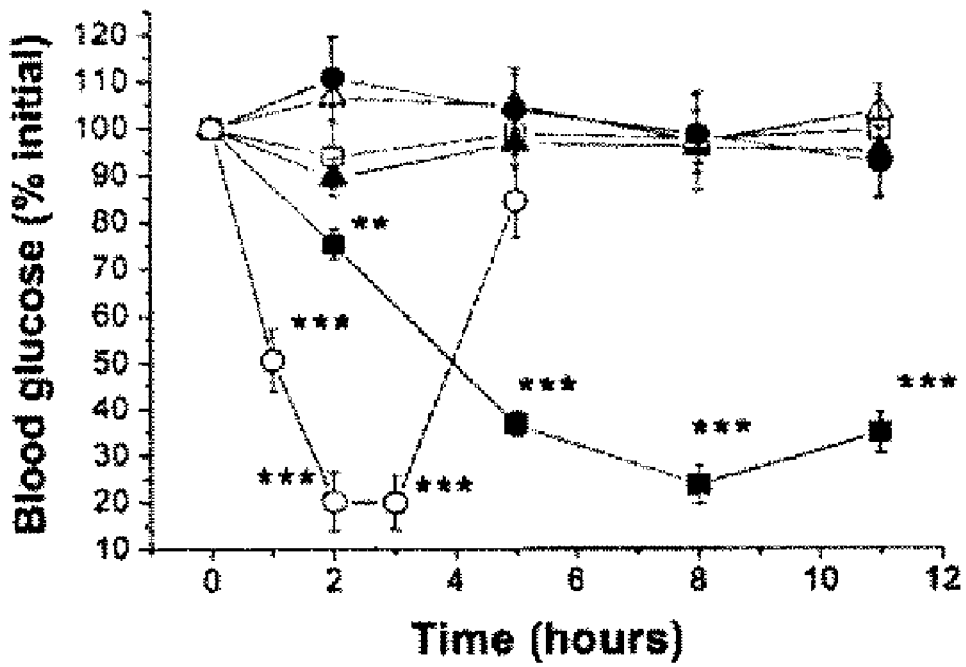

Moreover, these studies showed that TD-1 without insulin had no effect on either blood glucose or serum insulin level, indicating that the glucose-lowering effect observed with the TD-1 and insulin co-administration was due to the delivered exogenous insulin and not some unknown physiological response elicited by TD-1 (symbol ● in FIGS. 2B and 2C). In comparison, subcutaneous injection of insulin (14 μg) resulted in a rapid and short-lasting insulin-elevating and glucose-lowering effect, with the peak effect observed at between 2 and 3 hours after the co-administration and lasted for less than 5 hours (symbol ○ in FIGS. 2B and C).

Figure 2D:
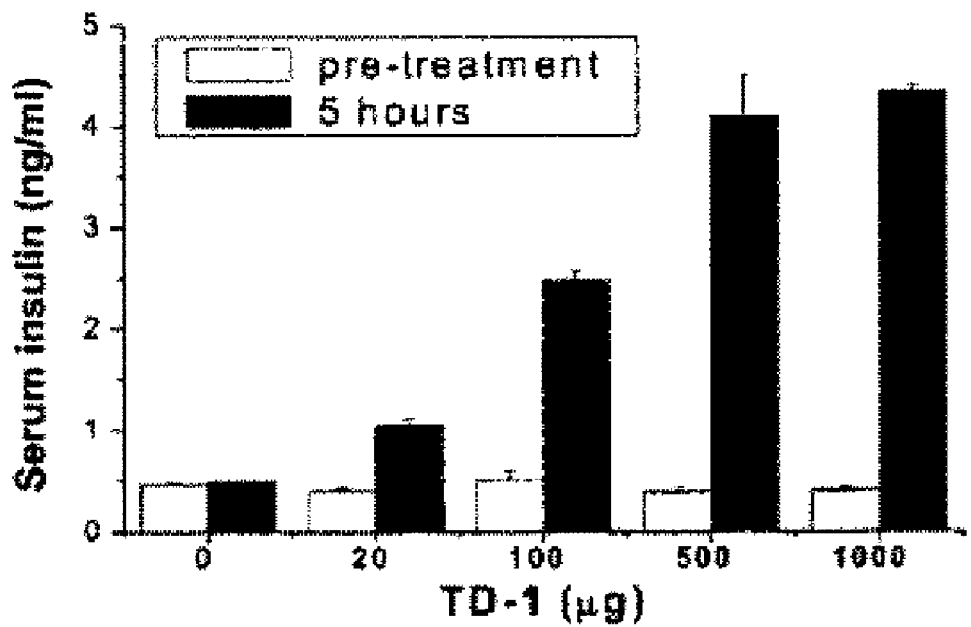
Figure 2E:
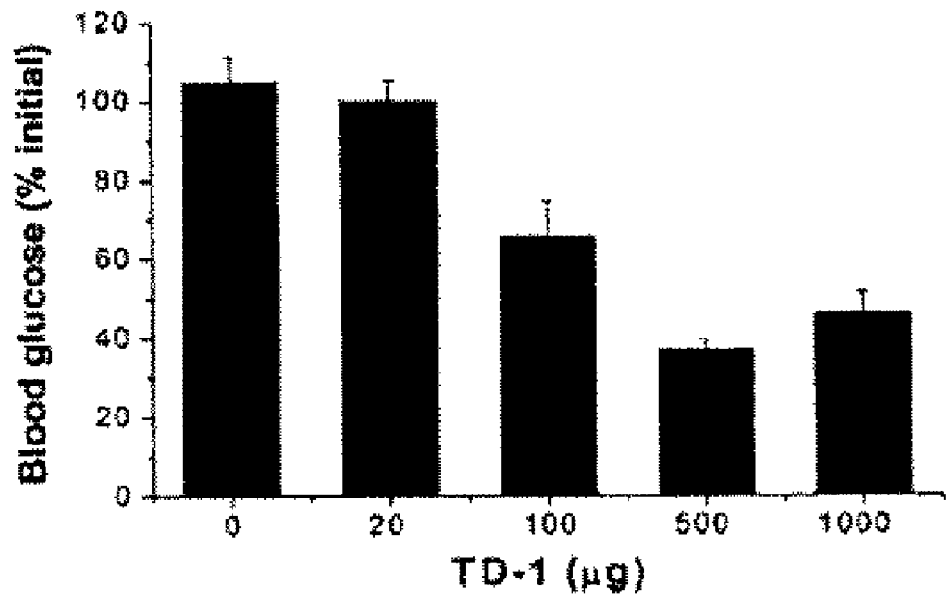
Figure 2F:
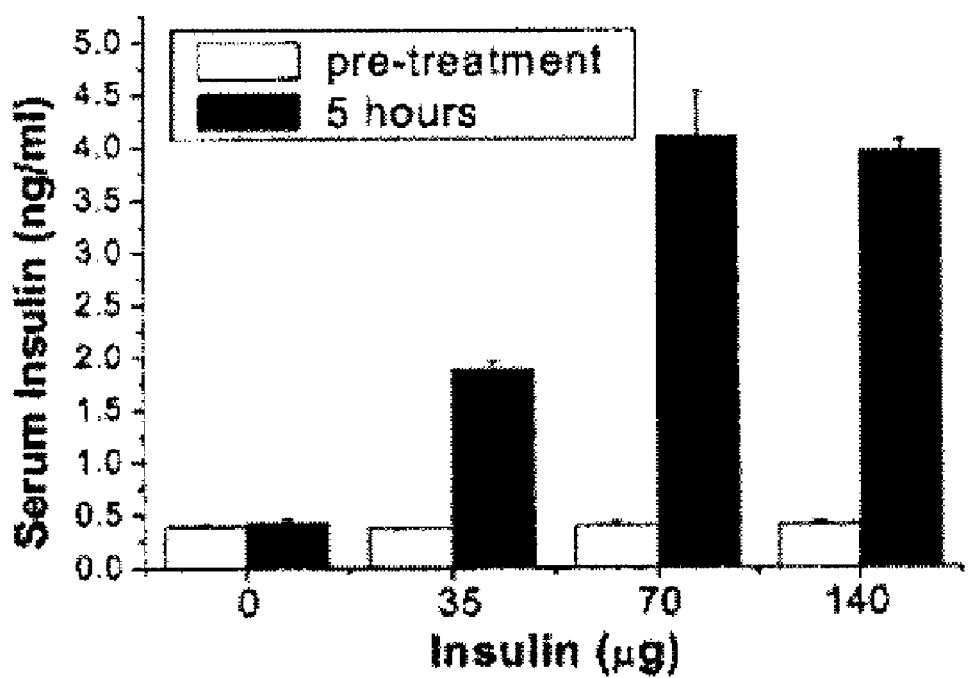
Figure 2G:
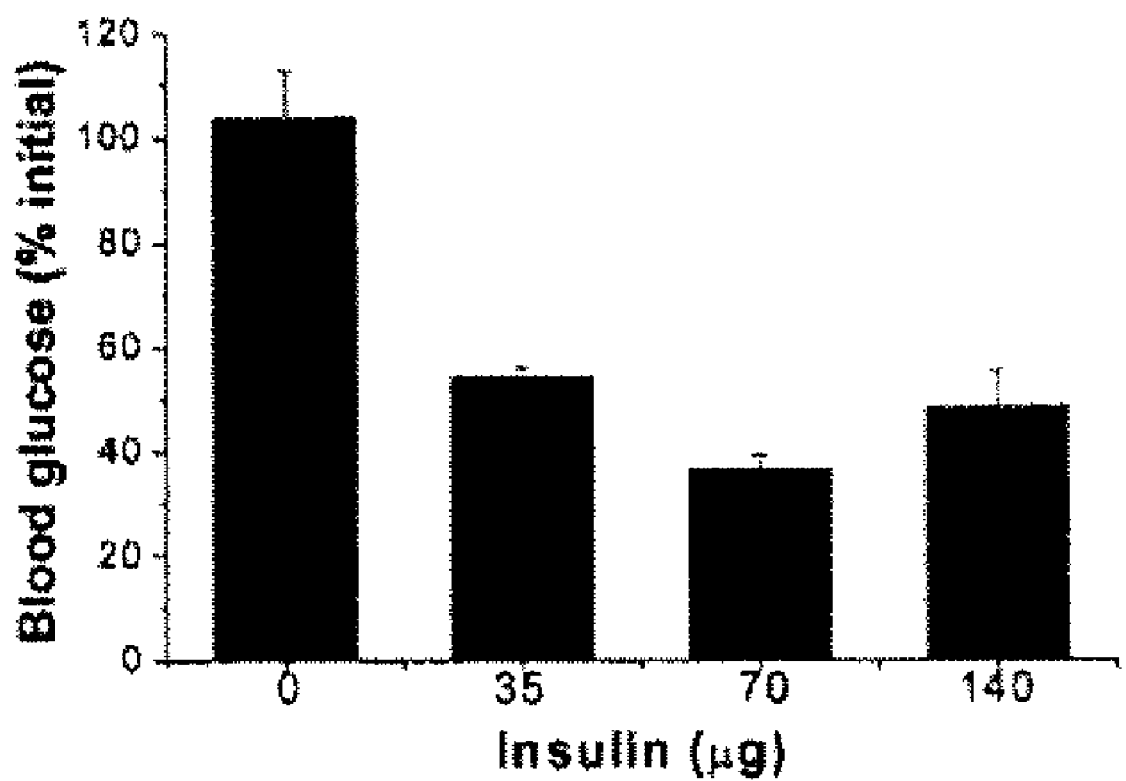

Furthermore, these studies indicated that the ability of TD-1 on transdermal delivery of insulin is dose-dependent. These studies showed that TD-1 at amounts of <20 μg, when topically co-administered with 70 μg of insulin, did not have significant insulin-elevating and glucose-lowering effect, while at >500 μg the transdermal-enhancing effect of TD-1 reached maximum (FIGS. 2D and 2E). A dose-dependent effect was also observed with insulin. With co-administered TD-1 fixed at 500 μg, 35 μg of insulin was sufficient to significantly enhance serum insulin and lower blood glucose level, but 70 μg or more of insulin is needed to achieve the maximum response (FIGS. 2G and 2F).

For insulin delivery, the various groups except the subcutaneous treatment group were compared to the TD-1 alone treatment group on each time point, using independent samples t-test. For the subcutaneous treatment group, each time point after co-administration was compared to the 0 hour data, using paired t-test.

Example 5

Enhancing Transdermal Delivery of a Growth Hormone by TD-1

Growth hormone delivery: To assess whether TD-1 can deliver a different protein drug, a recombinant human growth hormone (hGH, 500 μg) and TD-1 were co-administered at two different doses to the abdominal skin of Wistar rats, which had been treated with dexamethasone (12.5 mg/kg) for two days. In particular, male Wistar rats were given daily subcutaneous injection of dexamethasone (12.5 mg/kg; Sigma). After 2 days of treatment they were randomly assigned to different treatment groups, with 3 to 4 rats for each group. In one of the groups, each rat received 500 μg of pharmaceutical-grade recombinant human growth hormone, that is 21.5 Kd full-length protein expressed in *E. coli* and purified to >95%, with a specific activity of 2.5 IU/mg; Rising Bio-tech, Shanghai, China) and either 100 μg or 500 μg of TD-1 in 100 μl saline (the ratio of hGH:TD-1 is 5:1 and 1:1, respectively), co-administered topically to the exposed rat abdominal skin. After the co-administration, blood was drawn from the rat tail vein at various time points: 0, 2, 5, and 8 hours, and the amount of growth hormone in the serum was assayed using ELISA (Diagnostic Systems Laboratories, Webster, Tex.). The various groups were compared to the saline+hGH group on each time point, using independent samples t-test.

Figure 3:
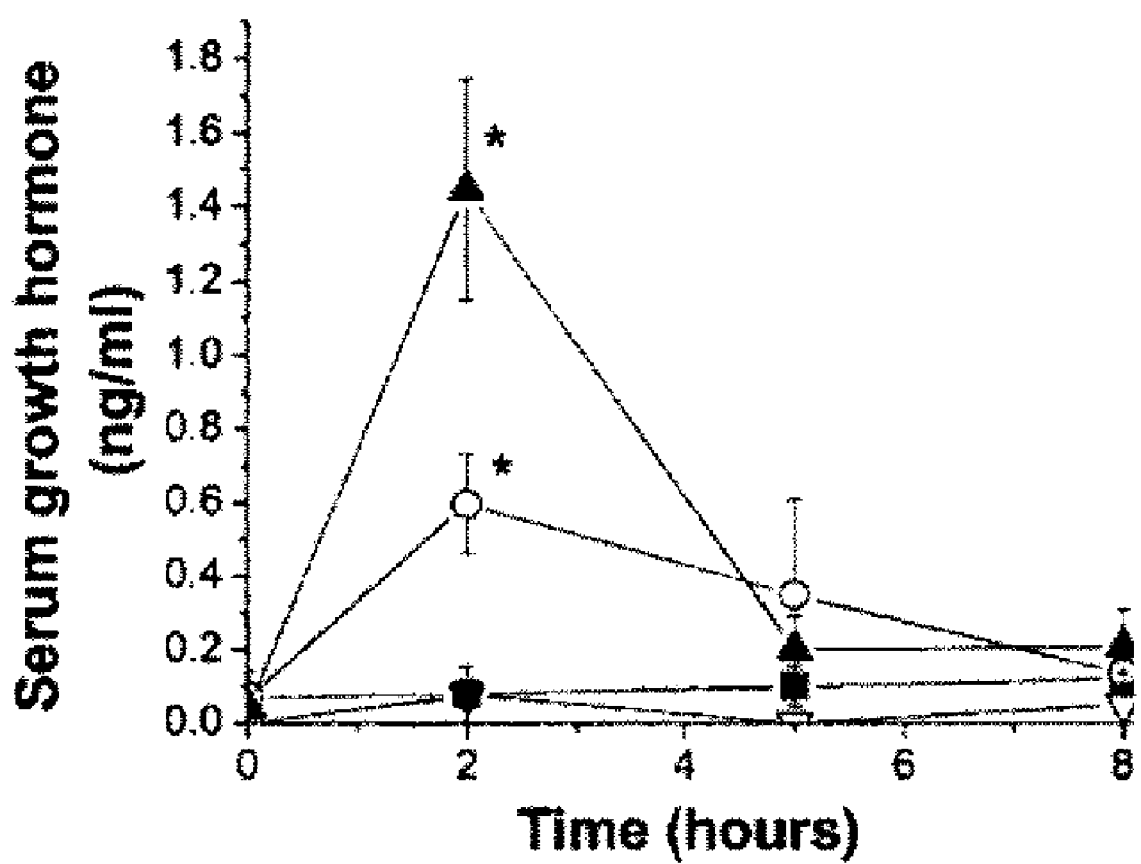
FIG. 3 illustrates transdermal delivery of human growth hormone. A recombinant human growth hormone (500 μg, >95% pure) was topically co-administered to dexamethasone-treated rats with 100 μg TD-1 (Δ), 500 μg TD-1 (○), 100 μg AP-1 (■), or saline (A). At various time points after administration, serum growth harmone levels were measured using an ELISA kit. Mean values and the SEM are shown (n≧3). *$P<0.05$.

Because, as reported before, high-level dexamethasone treatment effectively lowered the endogenous growth hormone of the rats to undetectable levels (Kolonin et al., 2004, Nature Med. 10:625, and Karande et al., 2004, Nature Biotech. 22:192), the exogenous transdermally delivered hGH can be easily detected in these dexamethasone-treated rats. The studies described herein showed that both 100 μg (Δ) and 500 μg (○) of TD-1 enabled hGH to reach systemic circulation, with significant amounts achieved at 2 hours after co-administration (FIG. 3). The 100 μg TD-1 showed more effective than 500 μg TD-1, indicating that the ratio of TD-1 and hGH may be important for transdermal delivery of hGH. In contrast, when co-administering the hGH with the controlled phage peptide, AP-1, the hGH in the systemic circulation was undetetable, indicating that AP-1 had no ability to deliver the hGH transdermally.

Example 6

Enhancing Transdermal Delivery of Apomorphin (APO) by TD-1

Apomorphine delivery: Apomorphine (APO) is a drug with indications for Parkinson's disease (Hagell et al., 2001, J. Neurosci. Nurs. 33:37) and sexual dysfunction (Montorsi, 2002, European Urology Supplements 1:4). Apomorphine HCl is a dopamine receptor agonist working centrally in the brain and spinal cord to stimulate release of dopamine (Anden et al., 1967, J. Pharm. Pharmacol. 19:627). It is reported that APO is involved in pleasure sensations and in the erection response. Its molecular formula is $C_{17}H_{17}NO_2 \cdot HCl \cdot \frac{1}{2}H_2O$ and molecular weight is 312.8 KD.

The transdermal-enhancing effect of TD-1 on APO transdermal delivery was tested in male Sprague-Dawley rats that weigh 200-250 g and were kept on a 12 hour on/off light cycle with food and water ad libitum. All behavioral studies were performed from 9:00 am to 4:00 pm at 24±1° C. While the animals were anesthetized with Urethane, the hair in an area of approximately 3.0 cm×3.0 cm in the interscapular region was carefully trimmed using scissors, with caution not to damage the skin (rats with any visible sign of skin damage were not used). Rats were allowed to recover for at least 24 hours before the experiments. One hundred ul cream containing indicated amounts of apomorphine (APO) was placed on the exposed skin and spread evenly using the side of a pipet tip. The cream formulation contains: glyceryl monostearate (7.5% by weight), hydroxypropyl methylcellulose (0.5% by weight), isopropyl myristate (10% by weight), methylparaben (0.5% by weight), propylparaben (0.5% by weight), polyxyl-40-stearat (11% by weight), saline (70% by weight), and various doses of APO and TD-1 that were coadministered.

Immediately after administration, rats were placed into individual polystyrene cages (32 cm long, 30 cm wide, 30 cm high) for behavioral observation. Rats were observed for 2 h and the number of penile erections (PE) was recorded by two observers. According to methods described by Berendsen and Broekkamp (1987, Eur. J. Pharmacol. 135(3):279-87), a penile erection was present when the following is observed: repeated pelvic thrust immediately followed by an upright position, an emerging engorged penis which the rat licks while eating the ejaculate.

Figure 4:
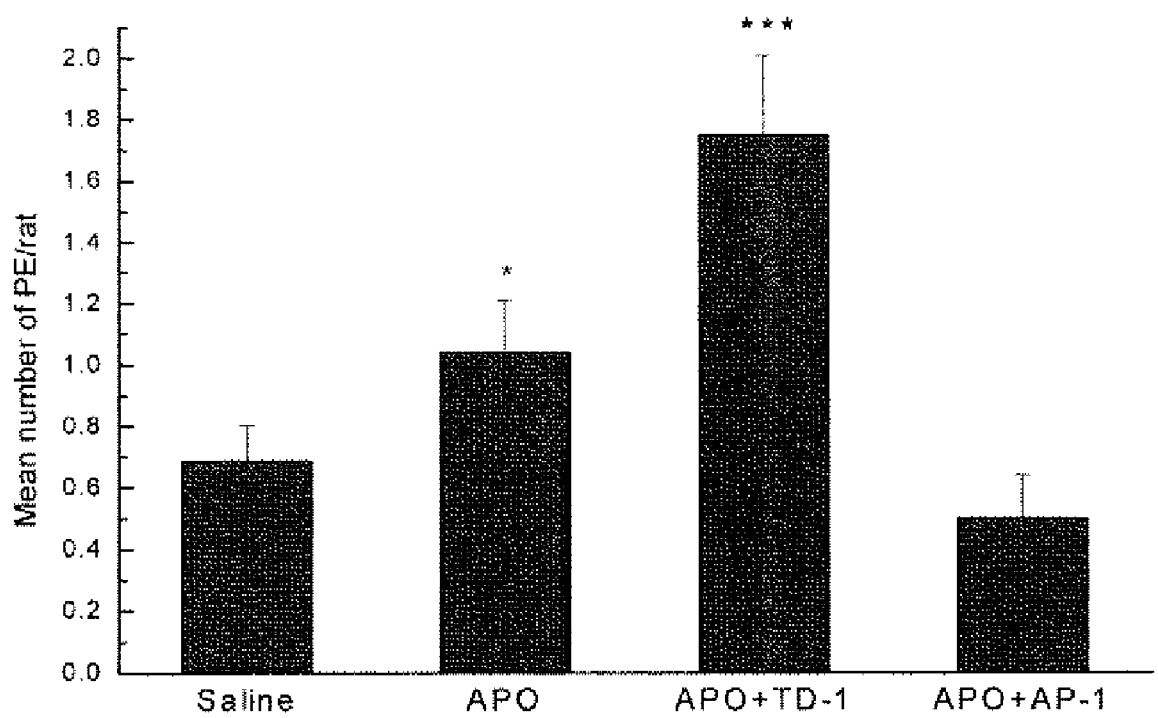
FIG. 4 illustrates that topically co-administered TD-1 facilitates transdermal apomorphine (APO) delivery. APO (0.8 mg/kg) was co-administered with TD-1 (2.0 mg/kg) or with AP-1 (2.0 mg/kg). *$P<0.05$ ***$P<0.0005$ (n=32).
Figure 5:
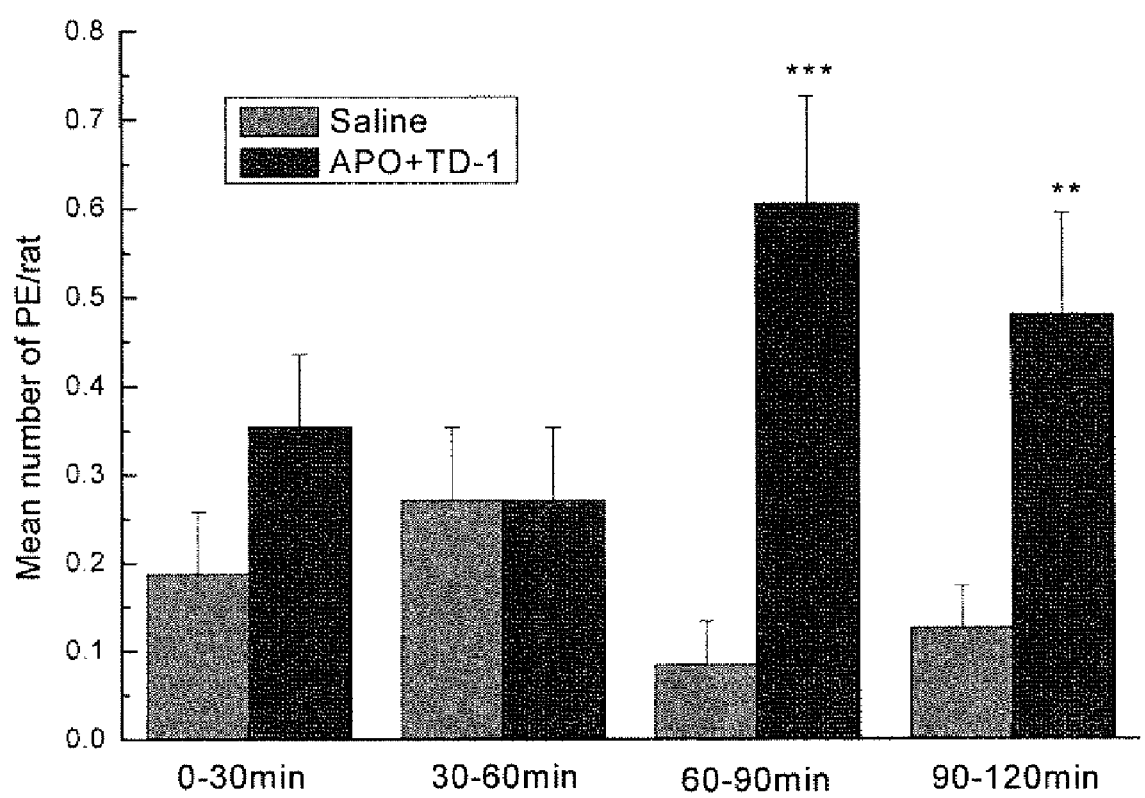
FIG. 5 shows time segment analysis of transdermally delivering APO with TD-1. APO (0.8 mg/kg) was co-administered with TD-1 (2.0 mg/kg), and numbers of APO-induced penile erections were measured at different time intervals: 0-30 min, 30-60 min, 60-90 min and 90-120 min. Mean values and the SEM are shown (n=32), $P<0.005$, *$P<0.0005$. The results indicate that most APO-induced penile erections occurred during the second hour after transdermal administration of APO.

FIG. 4 shows that topically co-administered TD-1 at the dose of 2.0 mg/kg with APO at the dose of 0.8 mg/kg facilitates transdermal APO delivery, whereas co-administered AP-1 at the same dose of 2.0 mg/kg showed no effect on APO transdermal delivery. Time segment analysis revealed that, after transdermally co-administering APO (0.8 mg/kg) and TD-1 (2.0 mg/kg), most PEs occurred during the second hour after the co-administration (FIG. 5).

Figure 6:
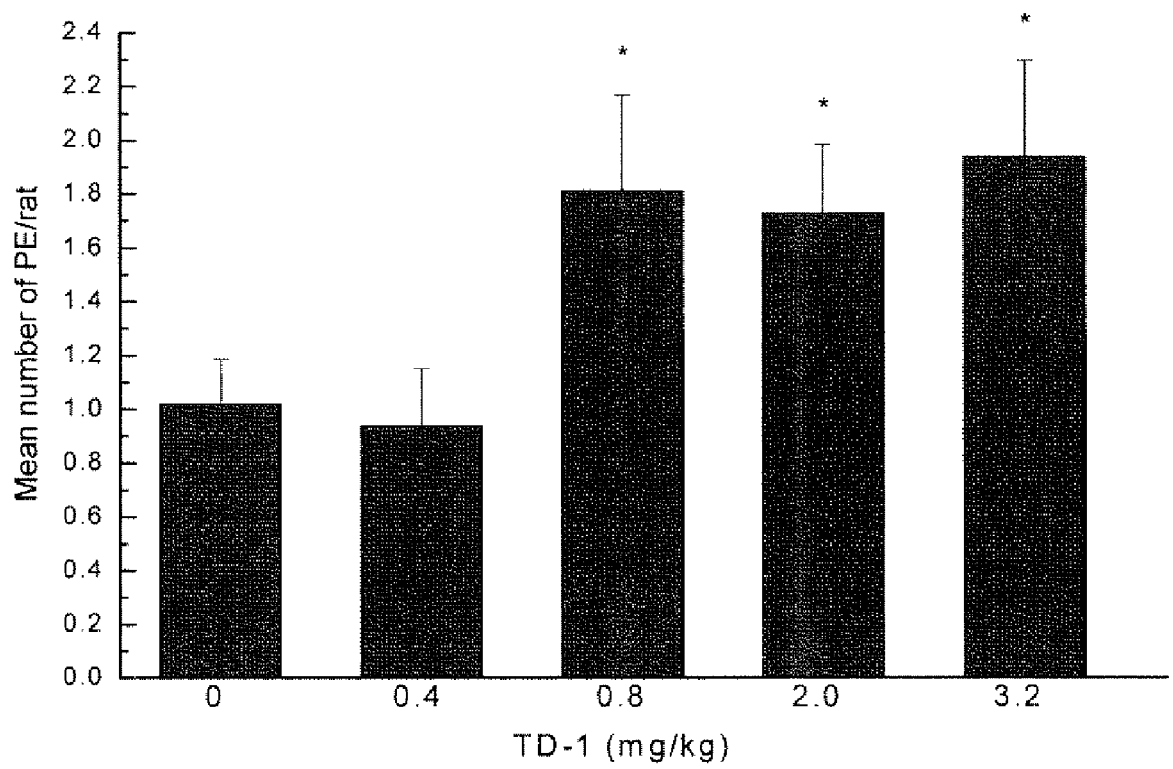
FIG. 6 illustrates TD-1 dose response with co-administration of APO. APO (0.8 mg/kg) was co-administered with TD-1 at amounts of 0 mg/kg, 0.4 mg/kg, 0.8 mg/kg, 2.0 mg/kg and 3.2 mg/kg. The numbers of APO-induced PEs were measured after the co-administration at each dosage. Mean values and the SEM are shown (n=32), *$P<0.05$.
Figure 7:
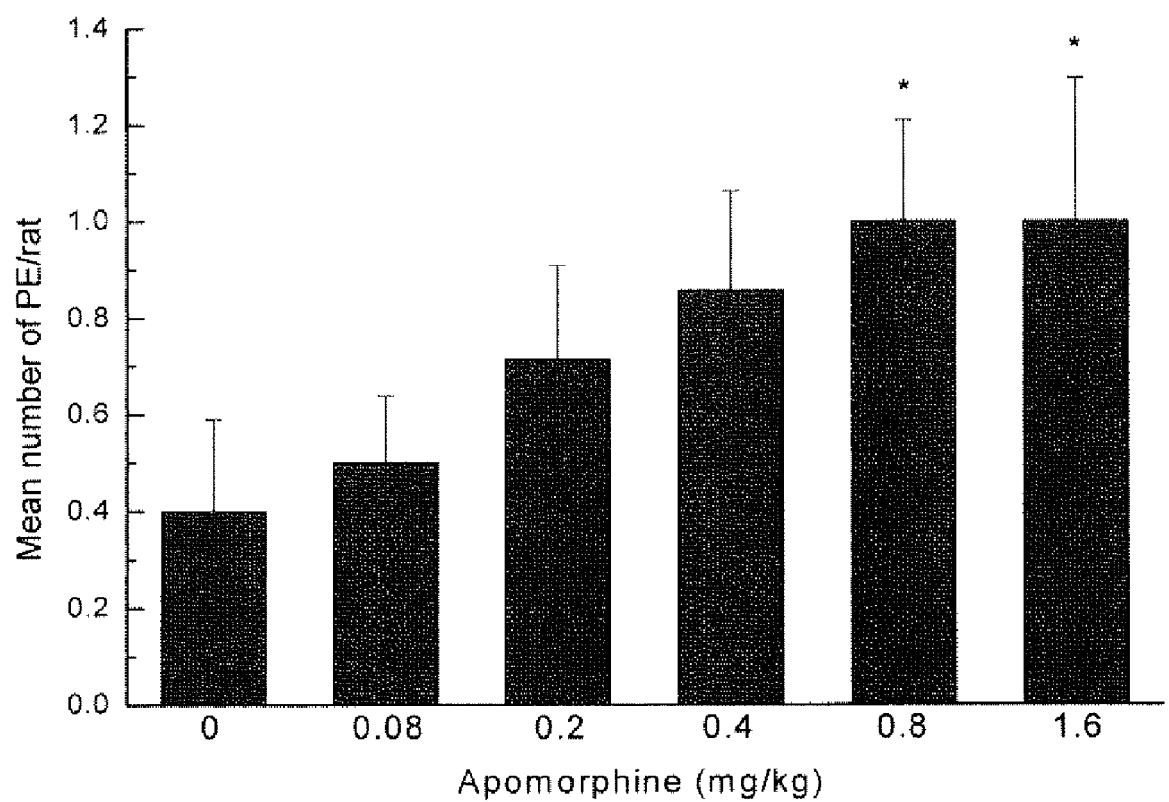
FIG. 7 illustrates APO dose response with co-administration of TD-1. TD-1 (0.8 mg/kg) was co-administered with APO at dose of 0 mg/kg, 0.08 mg/kg, 0.2 mg/kg, 0.4 mg/kg, 0.8 mg/kg and 1.6 mg/kg. The numbers of APO-induced PEs were measured after the co-administration at each dosage. Mean values and the SEM are shown (n=14), *$P<0.05$.

In addition, the studies described herein showed that the ability of TD-1 on transdermal delivery of APO is dose-dependent. The studies showed that TD-1 at the dose of 0.4 mg/kg, when topically co-administered with 0.8 mg/kg of APO, did not significantly increase the number of PEs in rats, while the transdermal-enhancing effect of TD-1 reached maximum at the doses of 0.8 mg/kg, 2.0 mg/kg and 3.2 mg/kg, respectively (FIG. 6). A dose-dependent effect was also observed with APO. With co-administered TD-1 fixed at 0.8 mg/kg, at least 0.8 mg/kg APO was needed to achieve the maximum response in increasing the numbers of PEs in rats, while APO at the doses of 0.4 mg/kg or below had no significant effect in increasing the numbers of PEs in rats (FIG. 7).

Example 7

Enhancing Transdermal Delivery of PT-141 by TD-1

PT-141 delivery: PT-141, developed by Palatin Technologies, Inc. (Cranbury, N.J.), is a peptide of seven amino acids: Ac-Nle-Asp-His-D-Phe-Arg-Trp-Lys-OH (SEQ ID NO:14). As a peptide analogue of α-melanocyte-stimulating hormone, PT-141 binds and activates central melanocortin receptors and selectively stimulates solicitational behavirors in the female rats (Pfaus et al., 2004, Proc. Nat. Acad. Sci. 101(27): 10201-204). Early clinical studies indicate that PT-141 is effective in treating a broad range of patients suffering from erectile dysfunction and femal sexual dysfunction (FSD) (Diamond et al., 2005, Urology 65(4):755-59).

The transdermal-enhancing effect of TD-1 on PT-141 transdermal delivery was also tested in male Sprague-Dawley rats that weigh 200-250 g and were kept on a 12 hour on/off light cycle with food and water ad libitum. All behavioral studies were performed from 9:00 am to 4:00 pm at 24±1° C. While the animals were anesthetized with Urethane, the hair in an area of approximately 3.0 cm×3.0 cm in the interscapular region was carefully trimmed using scissors, with caution not to damage the skin (rats with any visible sign of skin damage were not used). Rats were allowed to recover for at least 24 hours before the experiments. One hundred ul cream containing indicated amounts of PT-141 was placed on the exposed skin and spread evenly using the side of a pipet tip. The cream formulation contains: glyceryl monostearate (7.5% by weight), hydroxypropyl methylcellulose (0.5% by weight), isopropyl myristate (10% by weight), methylparaben (0.5% by weight), propylparaben (0.5% by weight), polyxyl-40-stearat (11% by weight), saline (70% by weight), and various doses of PT-141 and TD-1 that were coadministered.

Testing rats were divided into four groups with each group contain 6 rats. The rats in the first group were administered only saline on their skin; the rats in the second group were administered only PT-141 at the amounts of 160 μg/kg on their skin; the rats in the third group rats were co-administered the control peptide AP-1 (SEQ ID NO:6) at the amounts of 240 μg/kg and the PT-141 at the amount of 160 μg/kg (the ratio of AP-1:PT-141 is 3:2) on their skin; and the rats in the fourth group were co-administered TD-1 at the amounts of 240 μg/kg and PT-141 at the amount of 160 μg/kg (the ratio of TD-1:PT-141 is 3:2) on their skin.

Immediately after administration, rats were placed into individual polystyrene cages (32 cm long, 30 cm wide, 30 cm high) for behavioral observation. Rats were observed for 1 h and the number of penile erections (PE), the number of chasing, and the number of mounting were recorded, respectively. According to methods described by Berendsen and Broekkamp (1987, Eur. J. Pharmacol. 135(3):279-87), a penile erection was present when the following is observed: repeated pelvic thrust immediately followed by an upright position, an emerging engorged penis which the rat licks while eating the ejaculate. In addition, chasing was observed when the male moves forward along the female's side with its mouth licking the female's genital area, while mounting was present when the male's both front feet are off the ground and plant on the female's rump without ejaculation (Naby et al., 1992, Horm. Behav. 26:24; Randy et al., 1995, Nature 378: 383).

Figure 8:
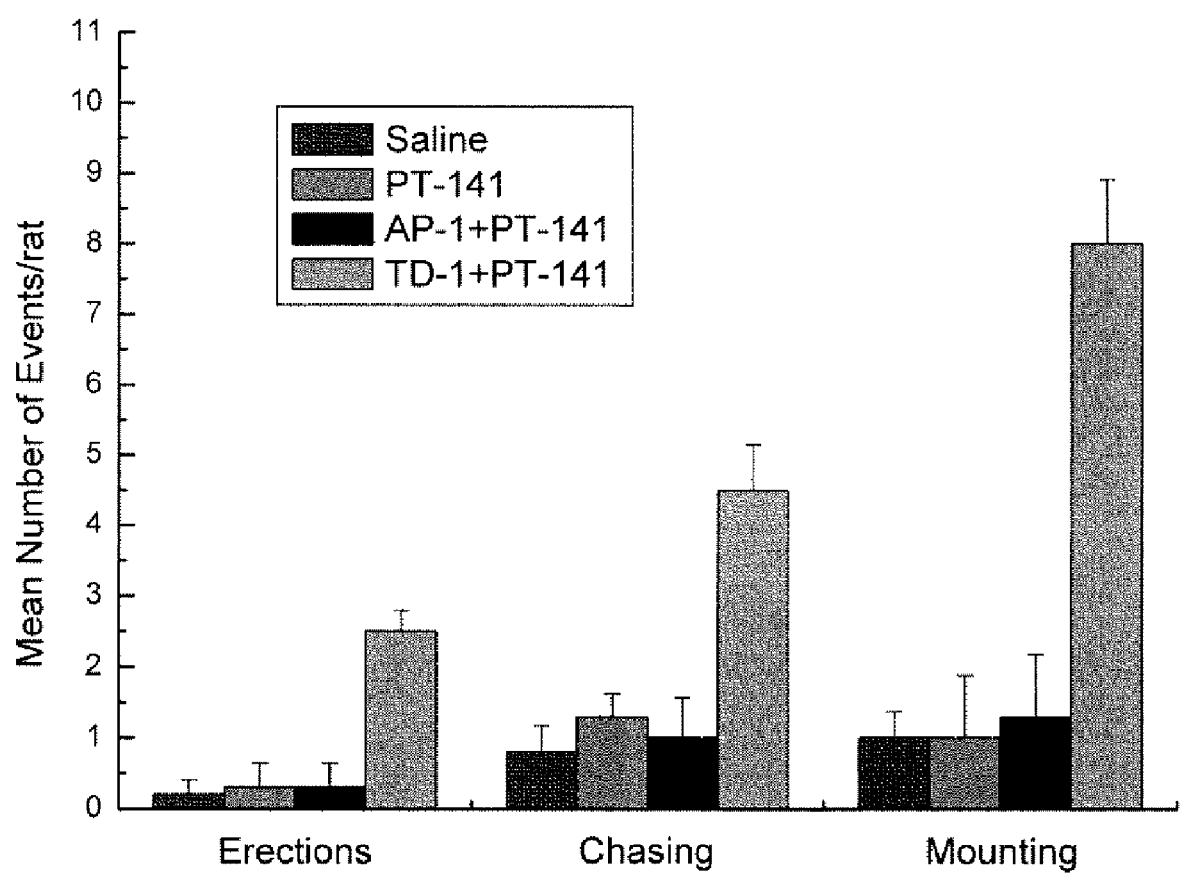
FIG. 8 illustrates TD-1 facilitating transdermal delivery of PT-141. PT-141 (160 μg/kg) was co-administered with TD-1 (240 μg/kg) and AP-1 (240 μg/kg), respectively. After one-hour observation, numbers of PT-141-induced PEs, chasing and mounting were measured separately. Mean values and the SEM are shown (n=6). ***$P<0.001$).

FIG. 8 illustrates that the transdermal delivery peptide, TD-1, facilitates transdermal delivery of PT-141. The administration of PT-141 alone and co-administration of the controlled phage peptide, AP-1, respectively, did not significantly increase the number of PEs, the number of chasing, and the number of mounting, indicating that PT-141 is not able to be transported through the skin by itself, and by AP-1 co-administration. However, the numbers of PEs, chasing and mounting were significantly increased when co-administering PT-141 with TD-1, indicating that TD-1 mediates and facilitates PT-141 transportation through skin, may be through deep follicular penetration.

Example 8

Figure 9A:
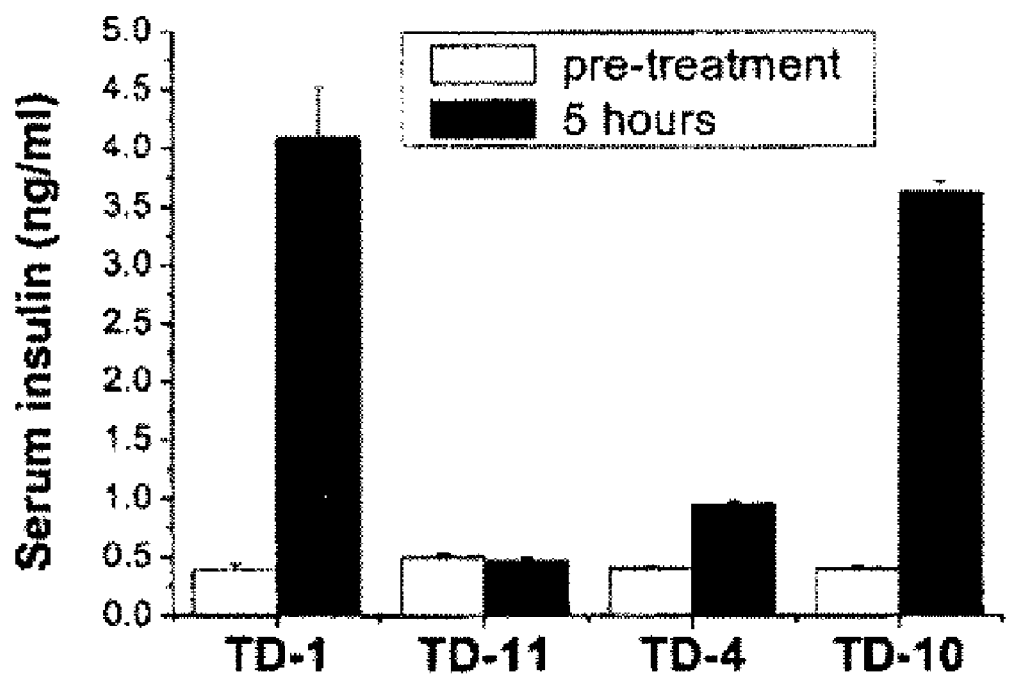
FIGS. 9A-9B show sequence specificity of TD-1 for facilitating transdermal delivery. TD-1 peptide analogs TD-4, TD-10, and TD-11 were chemically synthesized using conventional methods. TD-1 (500 μg) and its analog peptides TD-4 (500 μg), TD-10 (500 μg), and TD-11 (500 μg) were co-administered with insulin (70 μg) in 100 μl of saline, respectively. Serum insulin and blood glucose levels were measured before and 5 hours after coadministration and shown in FIGS. 9A and 9B, respectively. Mean values and the SEM are shown (n=6 for blood glucose level and n≧3 for serum insulin level).
Figure 9B:
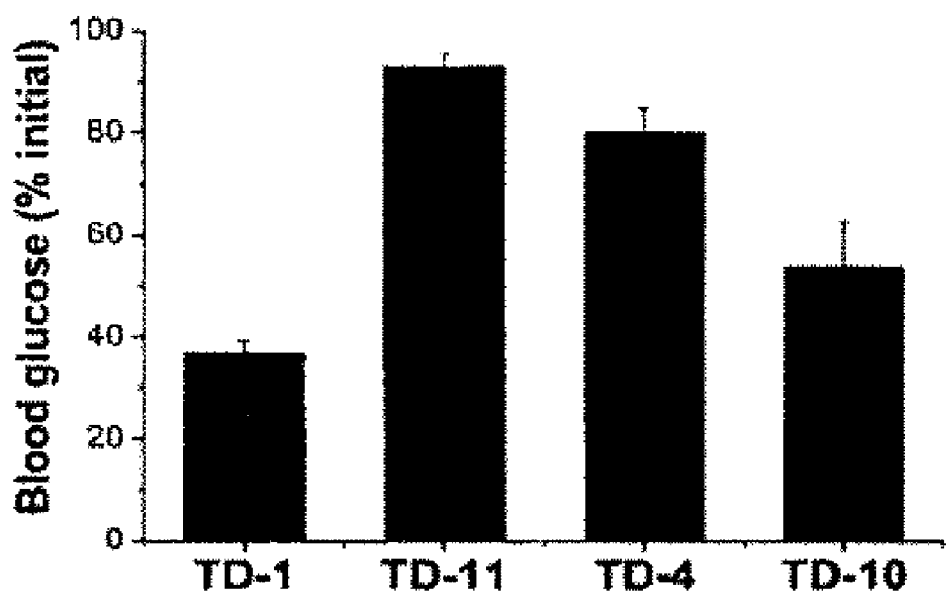

Chemical Synthesis of Peptide Analogs of TD-1 and their Effects on Insulin Transdermal Delivery To assess the sequence specificity of TD-1, several peptide analogs of TD-1 were chemically synthesized and tested for their ability to deliver insulin transdermally using the same methods as described above (Table 2). In particular, 500 μg of TD-1 variants and 70 μg of insulin were co-applied to the exposed abdominal skin (approximately 2 cm×2 cm) of diabetic rats in 100 μl saline. Blood glucose and serum insulin were measured before and 5 hrs. after the administration as described above.

constrained nature of TD-1 was important for transdermal activity (Table 2, FIGS. 9A & 9B). A partial alanine scan revealed that nearly every amino acid of the internal sequence is important for TD-1 's transdermal activity, as all alanine scan mutations, including TD-24, TD-2, TD-6, TD-22, and TD-23, resulted in a statistically significant loss of activity when compared to TD-1 (Table 2), but some amino acids are more important than others. Notably, K→D (TD-4) and P→A (TD-3) substitutions had the most effect among the point mutants and resulted in an almost completely loss of activity (Table 2, FIGS. 9A & 9B). On the other hand, the P→S (TD-10) substitution led to only a slight, insignificant decrease in activity (Table 2, FIGS. 9A & 9B). These results demonstrated that TD-1's transdermal activity is highly sequence specific.

Example 9

Transdermal Efficiency of Different Insulin Molecules and Time-lapse Effect of TD-1 on Transdermal Delivery of Insulin DLS measurements: To determine whether TD-1 mediates skin penetration by altering the molecular form of insulin, dynamic light-scattering studies (DLS) were performed. In particular, insulin (1 mg), with or without TD-1 (2.5 mg), was solubilized in 500 ml of saline in small scintillation glass vials and the pH was adjusted to 2.0 or 3.0 with 1 M HCl and 7.0 with 1 M NaOH. The solutions were transferred to a centrifuge tube and spun for 10 min at 10000 rpm. 40 μl of the supernatant were filtered by ANODISC™ membrane filter

TABLE 2

Transdermal activity of TD-1 peptide variants

| Peptide | Sequence | Blood Glucose[1] | | | | Serum Insulin[2] | | | |
|---|---|---|---|---|---|---|---|---|---|
| | | Mean[3] (%) | Range (%) | s.e.m (%) | P-value[4] | Mean[3] (ng/ml) | Range (ng/ml) | s.e.m (ng/ml) | P-value[4] |
| TD-1 | ACSSSPSKHCG (SEQ ID NO:2) | 38.68 | 38.05-44.48 | 2.04 | 1 | 3.9224 | 2.874-4.451 | 0.45633 | 1 |
| TD-2 | CSSSPSKHC (SEQ ID NO:1) | 68.44 | 58.76-70.31 | 6.64 | 0.0017 | 1.7480 | 1.654-1.881 | 0.0685 | 0.0092 |
| TD-11 | SSSPSKH (SEQ ID NO:5) | 92.93 | 86.28-102.6 | 3.07 | 0.0001 | 0.1938 | 0.162-0.252 | 0.0291 | 0.0012 |
| TD-24 | ACSASPSKHCG (SEQ ID NO:6) | 82.17 | 76.63-85.50 | 2.79 | 0.0002 | 0.7442 | 0.607-0.873 | 0.077 | 0.0024 |
| TD-3 | ACSSSASKHCG (SEQ ID NO:7) | 89.80 | 80.60-100.0 | 5.62 | 0.0012 | 0.4017 | 0.311-0.429 | 0.0677 | 0.0014 |
| TD-6 | ACSSSPAKHCG (SEQ ID NO:8) | 66.65 | 58.55-76.87 | 5.58 | 0.0158 | 1.6198 | 1.416-1.899 | 0.1446 | 0.0086 |
| TD-22 | ACSSSPSAHCG (SEQ ID NO:9) | 85.90 | 82.05-90.38 | 2.42 | 0.0001 | 0.7939 | 0.761-0.841 | 0.0241 | 0.0024 |
| TD-23 | ACSSSPSKACG (SEQ ID NO:10) | 81.36 | 74.17-85.53 | 3.61 | 0.0006 | 1.0422 | 0.813-1.265 | 0.1305 | 0.0037 |
| TD-10 | ACSSSSKHCG (SEQ ID NO:4) | 53.79 | 28.10-90.36 | 6.86 | 0.6654 | 3.4505 | 3.221-3.604 | 0.1165 | 0.3730 |
| TD-4 | ACSSSPSDHCG (SEQ ID NO:3) | 89.68 | 87.46-93.50 | 1.92 | 5.58E−5 | 0.7765 | 0.718-0.850 | 0.0389 | 0.0024 |

[1]5 hr value, expressed as % of the 0 hr value
[2]5 hr value minus 0 hr value
[3]n = 3, with the exception for the blood glucose of TD-1, TD-11, TD-10 and TD-4 (n = 6)
[4]Compared with TD-1 group on a two-tailed independent samples t-test The results showed that removing the termal A and G residues (TD-2) led to a significant loss of activity, as compared to TD-1 peptide. TD-11, a peptide consisting of only the internal seven-amino acid sequence of TD-1, was totally inactive for delivering insulin, suggesting that the disulfide with a pore size of 0.02 μm (Whatman International, Maidstone, UK) and taken for DLS measurement using DynaPro™ MS 800 (Wyatt technology Corporation/Protein Solutions, Santa Barbara, Calif.).

The results of DLS measurements are shown in Table 3.

TABLE 3

| pH | Sample | DLS measurements | | | | | |
|---|---|---|---|---|---|---|---|
| | | MW-R (Da) | | | Radius (nm) | | |
| | | Mean* | Range | s.e.m. | Mean* | Range | s.e.m. |
| 2.0 | Ins | 14585 | 13875-14961 | 356 | 1.9 | 1.8-1.9 | 0.033 |
| | Ins + TD-1 | 13615 | 13036-14129 | 317 | 1.8 | 1.8-1.8 | 0 |
| 3.0 | Ins | 20343 | 19816-20824 | 292 | 2.2 | 2.1-2.2 | 0.033 |
| | Ins + TD-1 | 21183 | 20488-21654 | 355 | 2.2 | 2.2-2.2 | 0 |
| 7.0 | Ins | 32328 | 30913-33841 | 847 | 2.6 | 2.6-2.7 | 0.033 |
| | Ins + TD-1 | 31155 | 29961-32361 | 693 | 2.6 | 2.5-2.6 | 0.033 |

*Average of three independent experiments

Figure 10A:
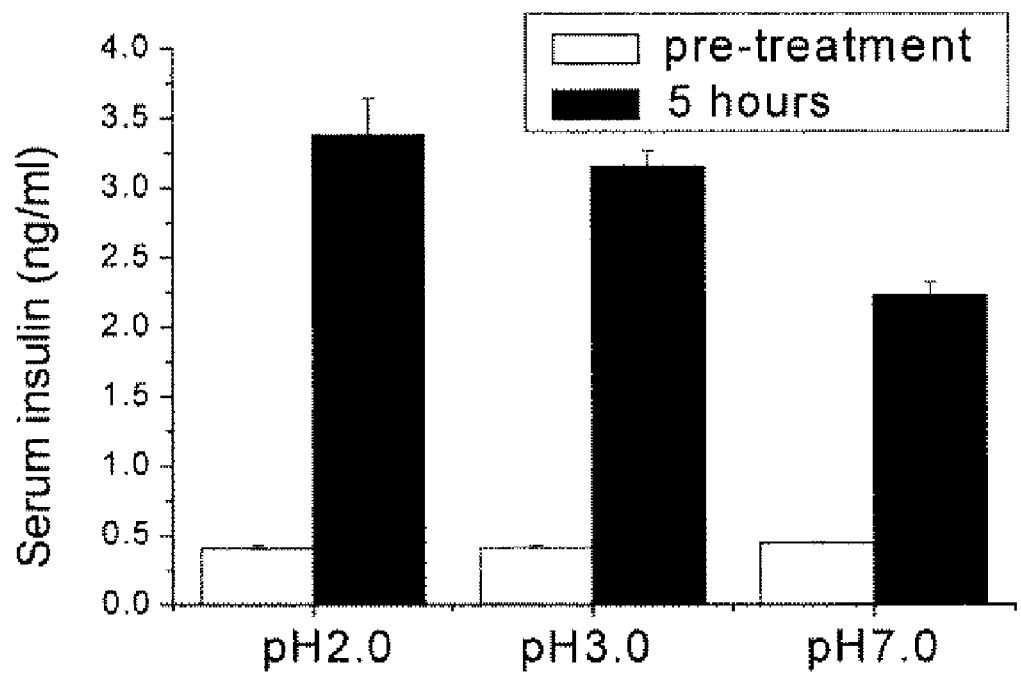
FIGS. 10a-10c show transdermal delivery efficiency of different molecular forms of insulin by TD-1, and time-lapse effect of TD-1, illustrating a possible mechanism of TD-1 in enhancing transdermal delivery of protein drugs.

In the absence of TD-1, insulin at pH 7.0 exhibited an apparent molecular weight of 32,328, consistent with a predominat hexamer form (Table 3). At pH 2.0, the observed molecular weight of insulin was 14,585, suggesting mostly a dimmer configuration, whereas at pH 3.0 (which is close to the pH value for an unadjusted TD-1/insulin mixture in saline) an intermediate molecular weight (20,343) was seen. Importantly, TD-1 did not significantly alter the apparent molecular weights of insulin under any of the three pH conditions. The radius data further supported this conclusion. The transdermal efficiency of insulin (mediated by TD-1) was similar at pH 2.0 (2.95-3.84 ng/ml) and 3.0 (2.85-3.42 ng/ml, p=0.39 compared to pH 2.0 group) and was about 20% lower at pH 7.0 compared with the pH 3.0 group (2.08-2.45 ng/ml) (Table 3, FIG. 10a). Some insulin precipitated at pH 7.0, which may have affected delivery of the drug at this pH. Overall, the different molecular forms of insulin did not appear to have a major effect on transdermal delivery facilitated by TD-1.

Figure 10B:
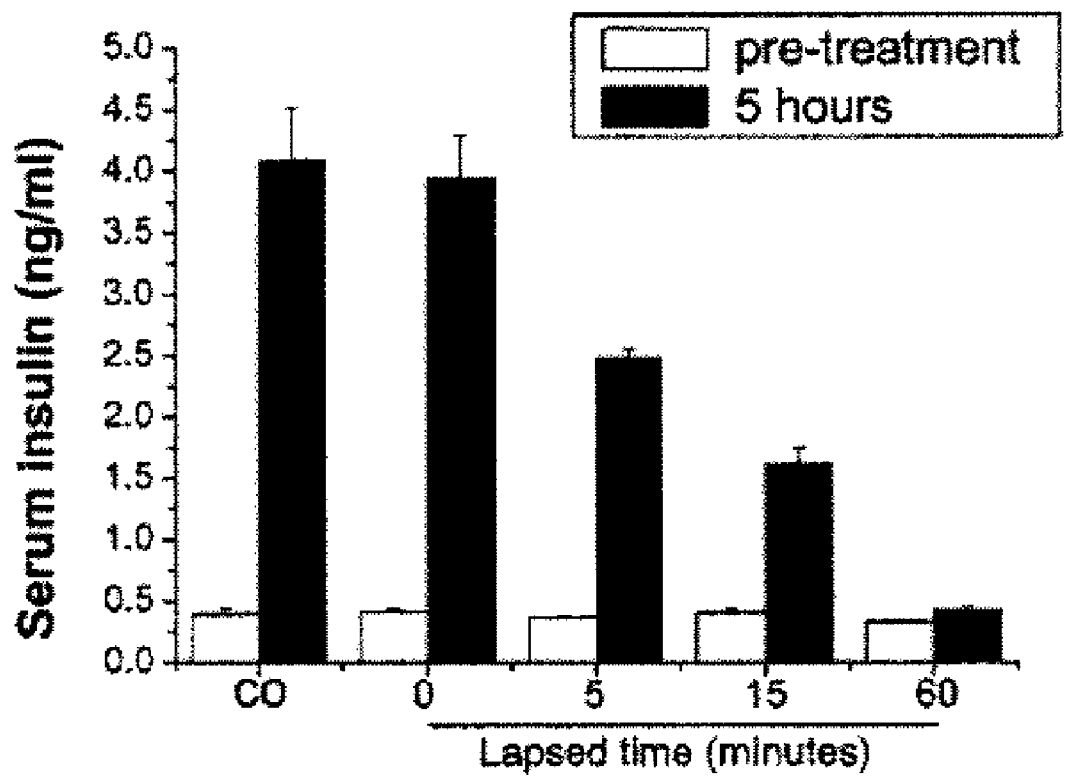
Figure 10C:
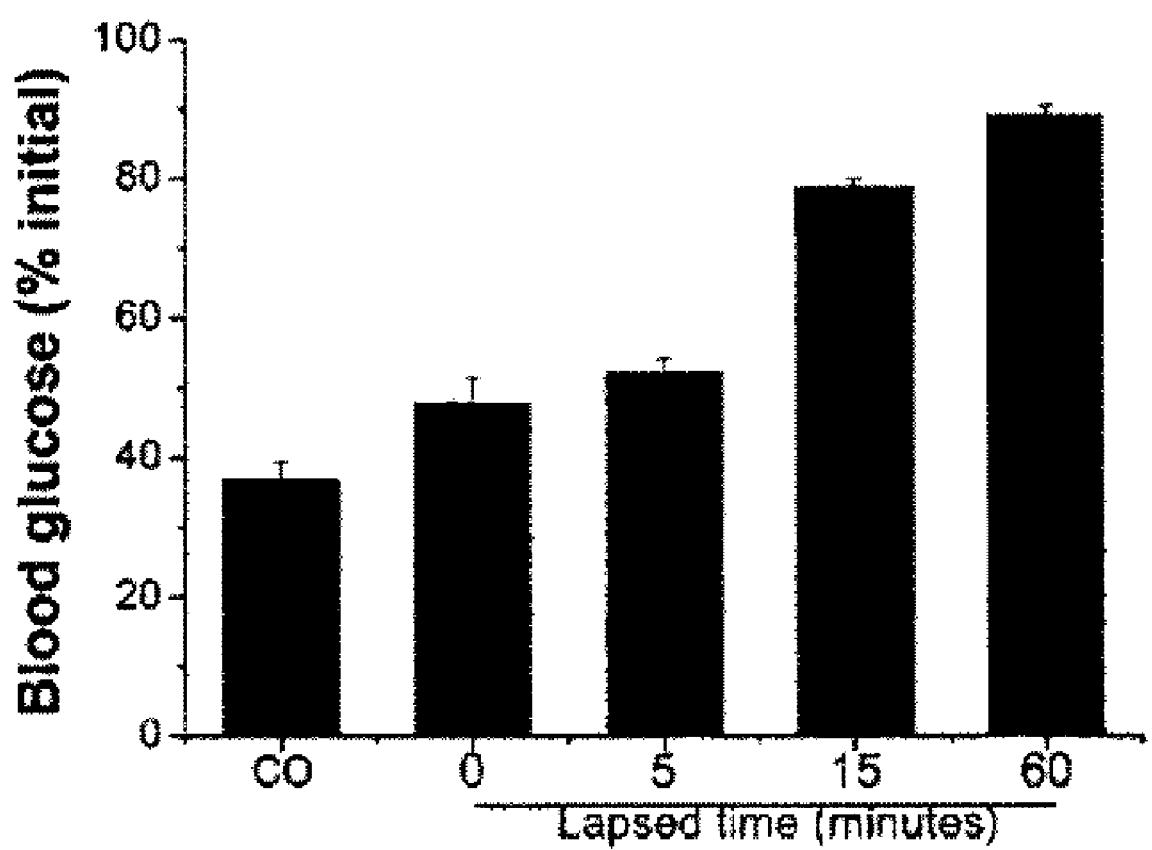

To further understand the mechanism of TD-1, time-lapse experiments were performed in which the skin of diabetic rats was pre-treated with TD-1 for 5 minutes. The TD-1 was then washed off and the rats were waited for a period of time before the administration of insulin to the same skin site. As judged by serum insulin levels (FIG. 10b), when there was no waiting period (the washing process took about 2 minutes), the transdermal efficiency of insulin was about the same as that observed under the TD-1 and insulin co-administration. A waiting time of 5 minutes still enabled a significant amount of insulin to reach blood circulation. But when the waiting period increased to 15 minutes or more, the transdermal efficiency of insulin dramatically decreased. Similar results were obtained with blood glucose measurement (FIG. 10c). These results indicated that TD-1 may have created a transient opening on the skin barrier to enable insulin to pass through and reach the systemic circulation.

Example 10

Follicular Penetration of Insulin-FITC Facilitated by TD-1

Microscopy of skin sections: To investigate the route of skin penetration for TD-1-mediated protein drug delivery, fluorescent microscopy of skin sections was performed after topical co-administration of TD-1 and insulin-fluorescein isothiocyanate (insulin-FITC). In particular, Insulin-FITC (Xi-an Huacheng, Xi-an, China) was dissolved in a small amount of DMF and subsequently diluted in saline for topical administration (final DMF concentration was <0.2%). Insulin-FITC (10 μg) mixed with or without TD-1 (100 μg) in a 100 μl saline solution was applied to the exposed abdominal skin of rats in the TD-1 treatment group and in the control group, respectively. For further comparison, 100 μl of 1:1 PBS:ethanol solution containing 10 μg insulin-FITC, 0.35% SLA and 0.15% PP SLA/PP treatment was administered to the exposed abdominal skin of rats in the SLA/PP treatment group. After 2 hours the skin was carefully cleaned by 70% isopropyl alcohol and harvested by dissecting. The isolated skin was fixed with ice-cold 4% paraformaldehyde in 0.1 M phosphate buffer (PH 7.4) overnight. Following several washes with 10 mM phosphate-buffered saline (PBS PH7.4), skin samples were immersed in PBS containing 4.5% sucrose for 24 hours and then dehydrated in 10 mM PBS containing 30% sucrose till deposition. Floating horizontal and vertical sections with a thickness of 20 μm were obtained on a freezing microtome (CM1900 LEICA, Heidelberger, Nussloch, Germany). Cryosections were mounted onto poly-L-lysine-coated glasses, dried at room temperature and enveloped with 10 μl VECTASHIELD Mounting Medium (Vector Laboratories, Burlingame, Calif.). Fluorescence photomicrographs of the sections were obtained with OLYMPUS IX-70 microscope (OLYMPUS, Tokyo, Japan) using a filter set having excitation and emission length at 490-495 nm and 520-530 nm, respectively. The same procedure was used to visualize skin penetration of TD-1-FITC and SC-1-FITC.

Figure 11:
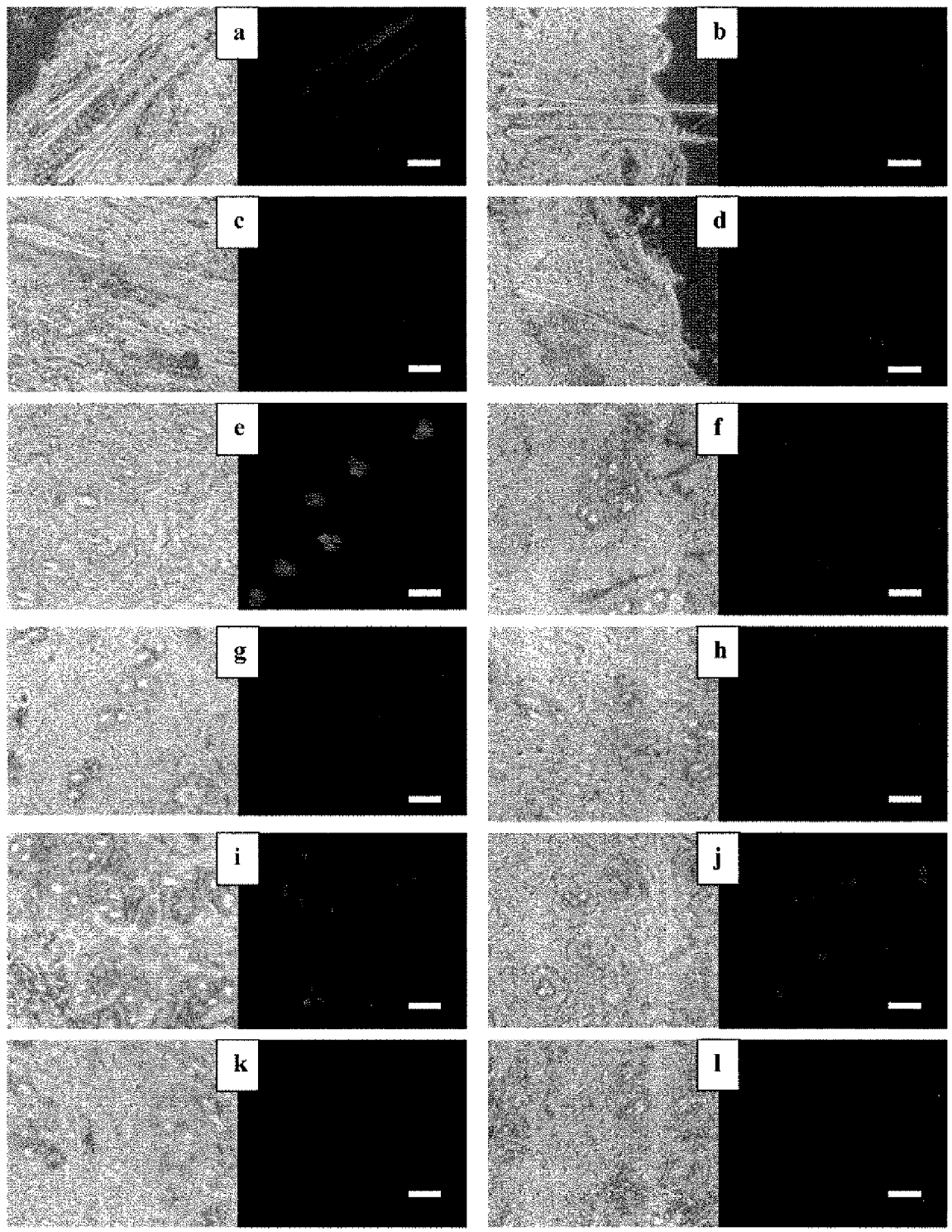
FIGS. 11(a)-11(l) illustrate hair follicle penetration of insulin-FITC. After topical administration to the abdominal skin of rats, vertical and horizontal (taken at ~600 μm below the skin surface) skin sections were examiner. Light and fluorescent microscope pictures are shown in tandem.
Figure 12:
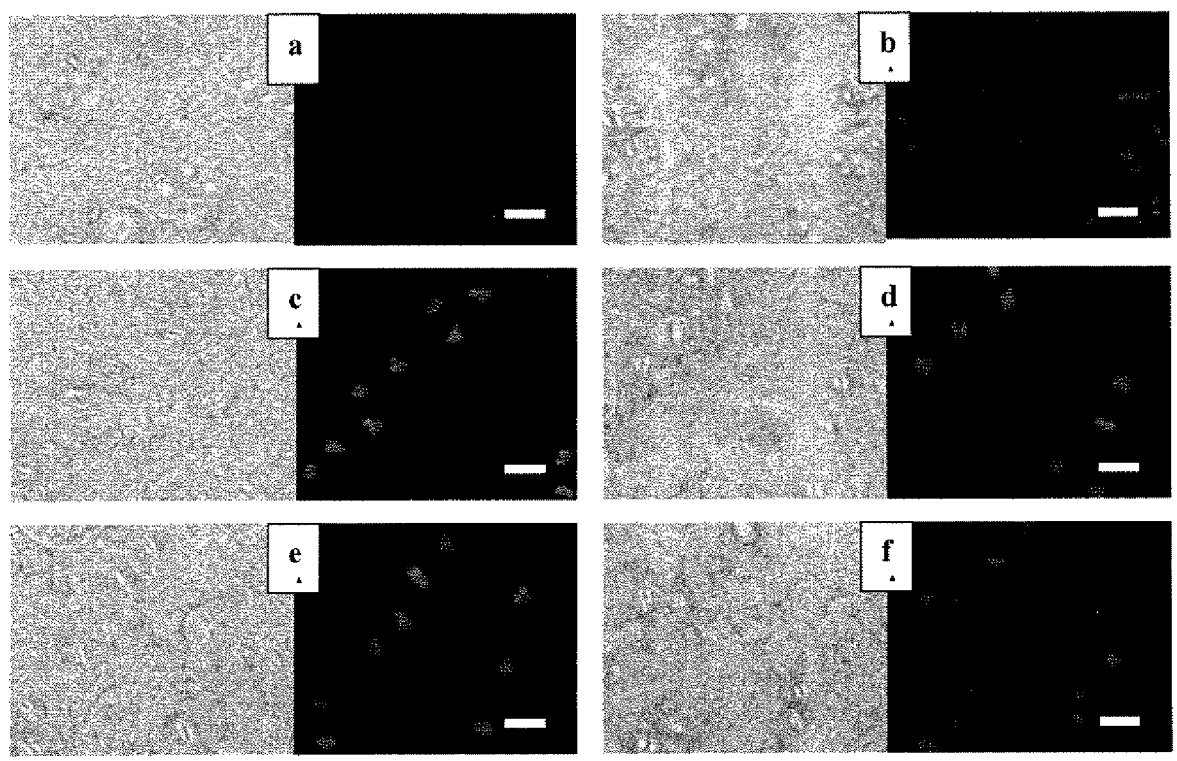
FIGS. 12a-12f show time course of hair follicle penetration of insulin-FITC. Insulin-FITC (10 μg) was topically co-administered with TD-1 (500 μg) to the exposed abdominal skin of SD-treated rats. After 0 minute (FIG. 12a), 30 minutes (FIG. 12b), 60 minutes (FIG. 12c), 2 hours (FIG. 12d), 5 hours (FIG. 12e), and 24 hours (FIG. 12f), horizontal skin sections (taken at approximately 600 μm below the skin surface) were visualized by light and fluorescent microscope. Magnification×200 (bar=100 μM).
Figure 13:
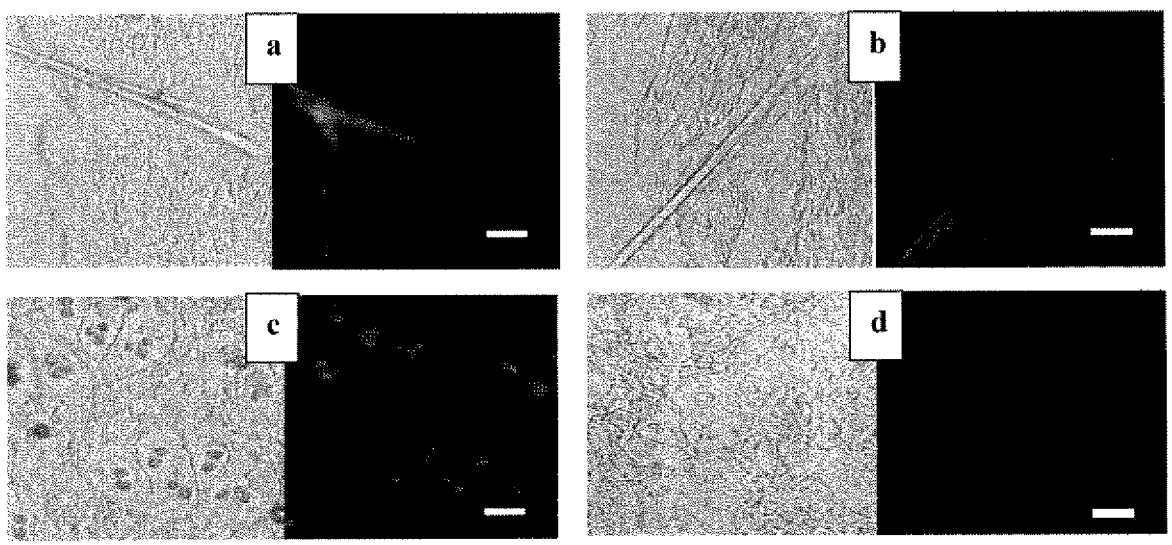
FIGS. 13a-13d illustrate hair follicle penetration of FITC-labeled TD-1 (TD-1-FITC) using light and fluorescent microscopy.

Vertical sectioning (sectioning perpendicular to the skin surface) revealed penetration of insulin-FITC deep into hair follicles (FIG. 11a). Little fluorescence was seen outside hair follicles. In the absence of TD-1, no follicle penetration was observed for insulin-FITC (FIG. 11c). In comparison, SLA/PP enabled penetration of insulin-FITC into both the hair follicles and the surrounding dermal tissue, but the amount and depth of follicular penetration were much less than that observed under TD-1 co-administration (FIG. 11d). These findings were backed up by the results of horizontal sectioning (sectioning parallel to the skin surface) at approximately 600 μm depth (FIGS. 11e, 11g and 11h). Time-course studies indicated that follicular penetration of insulin-FITC facilitated by TD-1 were detectable as early as 30 minutes post administration, reached a maximum at 2 hours and sustained for at least 24 hours (FIG. 12a to f). Deep follicular penetration of insulin was well correlated with systemic delivery of insulin. Co-administration of the control phage peptide AP-1, which did not facilitate transdermal insulin delivery, did not lead to follicular penetration of insulin-FITC (FIG. 11b and 11f). The time-lapse studies further supported this notion, as the length of the waiting period was inversely proportional to both the extent of follicular penetration of insulin-FITC (FIG. 11i-11l) and the amount of insulin delivered to the systemic circulation (FIG. 10b).

To assess whether TD-1 itself also enters hair follicles, fluorescent microscopy on skin sections was conducted after topical administration of FITC-labeled TD-1 (TD-1-FITC). Follicular penetration of TD-1-FITC, similar to that observed under insulin-FITC and TD-1 co-administration, was seen, but a control peptide (SC-1-FITC) did not show follicular penetration (FIG. 13a-13d).

Example 11

Determination of Hydrophilic Nature of TD-1 and Direct Assessment of TD-1 Interaction with Insulin Direct interaction assessment between TD-1 and $^{125}$I-insulin: ELISA plate wells were coated with indicated amounts of TD-1 dissolved in 50 mM NaHCO3, pH 9.6 (37° C., 2 h) and blocked with 1% BSA. $^{125}$I-insulin (~30,000 cpm) was added to each well and incubated for 2 h at 37° C. After extensive washing with PBST (PBS+0.1% Tween-20), radioactivity was measured with Gamma Radioimmunoassay Counter. For the control, a guinea pig anti-porcine insulin antibody (Atom High-Tech) at various dilutions was coated on plated and assessed for bind to $^{125}$I-insulin in the same way as described above.

Direct interaction assessment between TD-1 and insulin: ELISA plate wells were coated with 1 µg to 1 mg of TD-1 and then blocked with BSA as described in the previous section. Insulin (100 µg) and a guinea pig anti-porcine insulin antibody (Atom High-Tech, used at 1:1000 dilution), in 100 µl of PBS, was added to each well and incubated for 2 hrs. at 37° C. After washing 6× with PBST, the plate was incubated with 1:2000 dilution of anti-guinea pig IgG conjugated with HRP (Chang-Dao Biotechnology Co. Ltd., Shanghai, China) for 1 hr. at 37° C. The plate was washed 6× with PBST, followed by the addition of 100 µl/well of TMB substrate. After incubation at room temperature for 10 mins and additional of stop solution (1 M $H_2SO_4$), absorbance was read at 450/630 nm in an ELISA reader. As a positive control, 1 ng to 1 µg of insulin was coated directly on the plates and was detected by the same procedure as described above. In a reverse interaction scheme, ELISA plate wells were coated with 1 µg to 1 mg of insulin, blocked with BSA, incubated with TD-1-AngII fusion peptide (100 µg per well), incubated with rabbit polyclonal antibody against human angiotensin II (Atom High-Tech, used at 1:1000) and 1:2000 of anti-rabbit IgG conjugated with HRP (Zhong Shan Golden Bridge Biotechnology, Beijing, China), and finally assayed by TMB color reactionm using the same protocol as described above. The control for this reverse scheme experiment used 1 µg of TD-1-AngII coated directly to the wells.

Determination of octanol-water partition coefficient: n-Octanol and water were presaturated with each other by vigorous mixing and letting to stand at 25° C. for 24 h. 10 mg of TD-1 was transferred to a 15-ml screw-capped centrifuge tube, and pre-saturated octanol and water (2.5 ml each) were added. The mixture was vigorously shaken for 10 min, let to stand at 25° C. for 12 h, and then centrifuged (400 g, 10 min) to achieve good separation of two phases. TD-1 concentrations in the two phases were determined by HPLC and used to compute log $P_{ow}$. For HPLC, a 250×4.6 mm reverse C18 analytical column (COSMOSIL) was used with the mobile phase consisting of 30% acetonitrile/O/1% TFA and 70% water/0.1% TFA and a flow rate of 1 ml/min with an injection loop of 20 µl. Detection was at 230 nm.

Figure 14A:
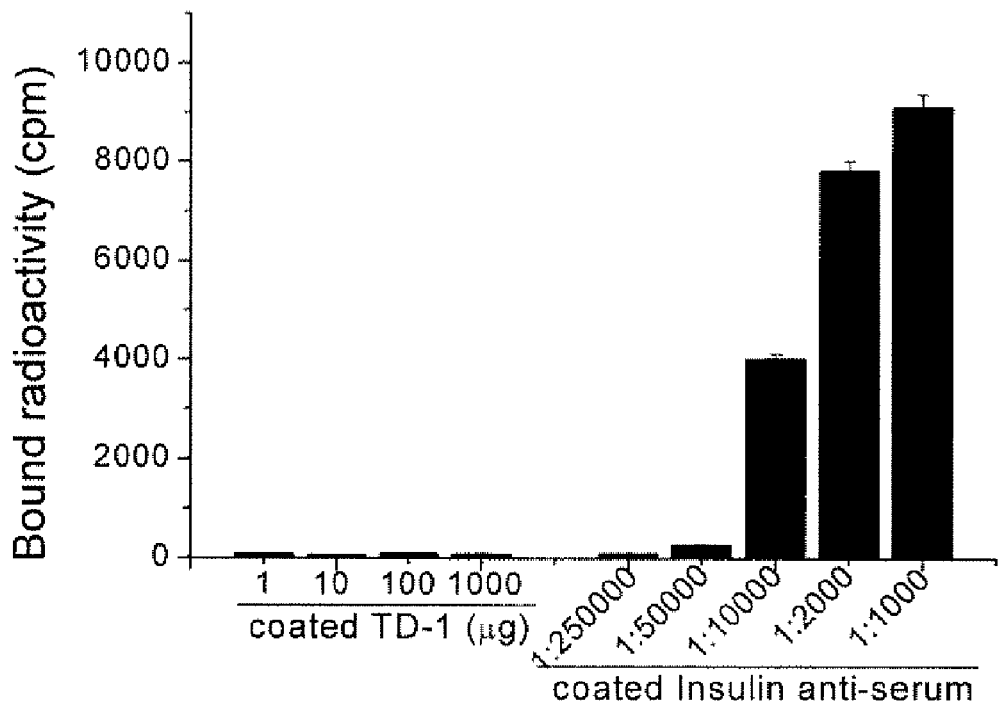
Figure 14B:
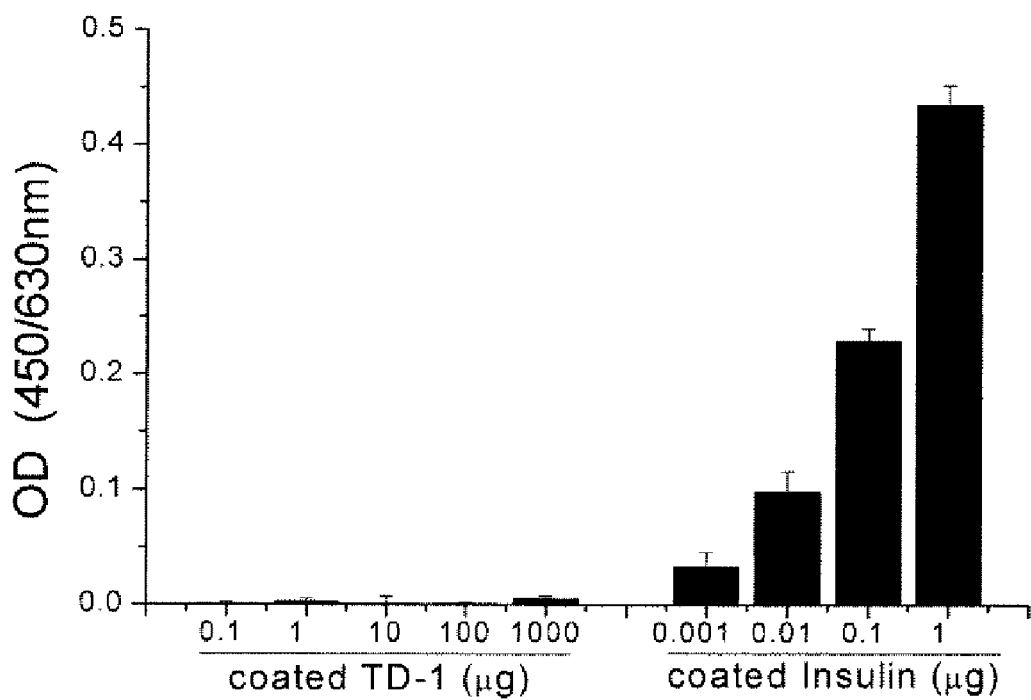

As the octanol/water partition coefficient (log Pow) for TD-1 was equal to −3.03, TD-1 is predicted to be highly hydrophilic with poor skin permeability based on various models on log $P_{ow}$. To further understand the working mechanism of TD-1, two types of direct binding assays were conducted as described above. In the first assay, $^{125}$I-insulin was added to enzyme-linked immunosorben assay (ELISA) microwell plates precoated with increasing amounts of TD-1 (up to 1 mg per well), and bound radioactivity was determined after washing. No significant radioactivity above the background level was detected at any TD-1 amount (FIG. 14a, left panel). In the control, precoating with increasing amounts of an insulin antibody resulted in increasing amounts of $^{125}$I-insulin bound to the wells, indicating that the coating and detection procedure was working (FIG. 14a, right panel). In the second assay, microwell plates were coated with increasing amounts of TD-1 and then incubated with insulin. Any bound insulin was then detected with a guinea pig anti-insulin antibody coupled with anti-guinea pig IgG conjugated with peroxidase. No significant amount of insulin was found to bind to precoated TD-1 (FIG. 14b, left panel), whereas as little as 1 ng of insulin directly coated on the microwell plate could be detected by the same procedure.

Figure 14C:
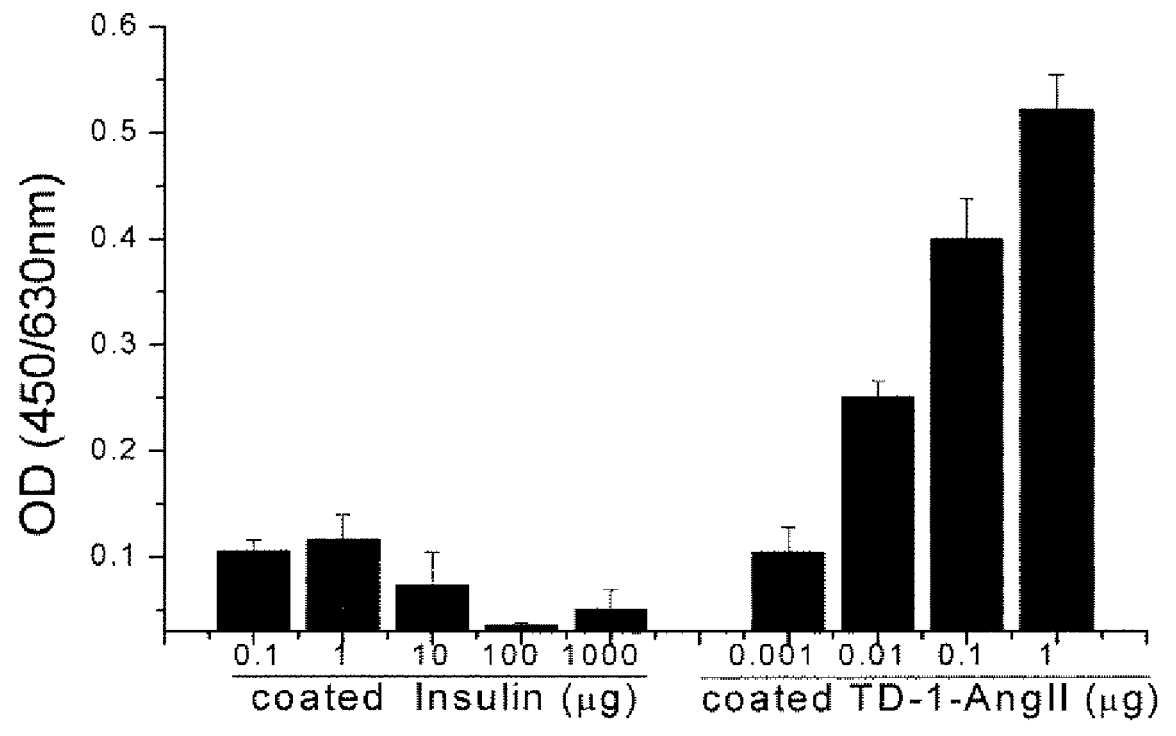

As described above, a reserve scheme of these experiments were also performed, in which the plates were precoated with increasing amounts of insulin and then incubated with TD-1-AngII, a fusion peptide composed of TD-1 and angiotensin II sequences. Any bound TD-1-AngII was then detected with a rabbit anti-angiotensin II antibody coupled with anti-rabbit IgG conjugated with peroxidase. No significant amount of TD-1-AngII was found to bind to precoated insulin (FIG. 14c, left panel), whereas as little as 10 ng of TD-1-AngII was detected by the same procedure. These results indicated that TD-1 does not bind insulin directly.

In summary, the studies presented herein demonstrated that TD-1 achieves efficient delivery to systemic circulation, while it does not need to be associated with the cargo to exert its delivery effect. The studies further demonstrated the feasibility of using phage display, a powerful molecular biology technique, for the identification of peptides with transdermal-enhancing activity, and TD-1 and analogs thereof may have broad application potential in both transdermal and topical drug delivery, especially for delivery of hydrophilic macromolecular drugs.

APPENDIX

| | |
|---|---|
| Amino acid sequence for TD-2:<br>CSSSPSKHC | (SEQ ID NO:1) |
| Amino acid sequence for TD-1:<br>ACSSSPSKHCG | (SEQ ID NO:2) |
| Amino acid sequence for TD-4:<br>ACSSSPSDHCG | (SEQ ID NO:3) |
| Amino acid sequence for TD-10:<br>ACSSSSSKHCG | (SEQ ID NO:4) |
| Amino acid sequence for TD-11:<br>SSSPSKH | (SEQ ID NO:5) |
| Amino acid sequence for TD-24:<br>ACSASPSKHCG | (SEQ ID NO:6) |
| Amino acid sequence for TD-3:<br>ACSSSASKHCG | (SEQ ID NO:7) |
| Amino acid sequence for TD-6:<br>ACSSSPAKHCG | (SEQ ID NO:8) |
| Amino acid sequence for TD-22:<br>ACSSSPSAHCG | (SEQ ID NO:9) |
| Amino acid sequence for TD-23:<br>ACSSSPSKACG | (SEQ ID NO:10) |
| Amino acid sequence for AP-1:<br>ACNATLPHQCG | (SEQ ID NO:11) |

APPENDIX-continued

Amino acid sequence for SC-1:  (SEQ ID NO:12)
HPGARPVFPWPG

Amino acid sequence for the  (SEQ ID NO:13)
conjugate: N$^a$-Fmoc-Ala-
Cys(Trt)-Ser(tBu)-Ser(tBu)-
Ser(tBu)-Pro-Ser(tBu)-Lys(Boc)-
His(Trt)-Cys(Trt)-Gly-resin APPENDIX-continued Amino acid sequence for PT-141:  (SEQ ID NO:14)
Ac-Nle-Asp-His-D-Phe-Arg-Trp-Lys-OH Amino acid sequence for a short  (SEQ ID NO:15)
linker sequence: Gly-Gly-Gly-Ser

---

We claim:

1. An isolated peptide having an amino acid sequence as set forth in SEQ ID NO:1 (TD-2), SEQ ID NO:2 (TD-1), or SEQ ID NO:4 (TD-10).

2. The peptide of claim 1, wherein said peptide has an amino acid sequence of SEQ ID NO:1 (TD-2).

3. The peptide of claim 1, wherein said peptide has an amino acid sequence of SEQ ID NO:2 (TD-1).

4. The peptide of claim 1, wherein said peptide has an amino acid sequence of SEQ ID NO:4 (TD-10).

5. The peptide of claim 1, wherein said peptide enhances transdermal delivery of a pharmaceutically active agent.

6. The peptide of claim 5, wherein said pharmaceutically active agent is selected from the group consisting of insulin, growth hormone, apomorphine, and PT-141.

7. The peptide of claim 5, wherein said pharmaceutically active agent is insulin.

8. A composition for transdermal delivery comprising a peptide having an amino acid sequence as set forth in SEQ ID NO:1 (TD-2), SEQ ID NO:2 (TD-1), or SEQ ID NO:4 (TD-10).

9. The composition of claim 8, wherein said peptide comprises an amino acid sequence of SEQ ID NO:1 (TD-2).

10. The composition of claim 8, wherein said peptide has an amino acid sequence of SEQ ID NO:2 (TD-1).

11. The composition of claim 8, wherein said peptide has an amino acid sequence of SEQ ID NO:4 (TD-10).

12. The composition of claim 8, further comprising a pharmaceutically active agent.

13. The composition of claim 12, wherein said pharmaceutically active agent is selected from the group consisting of insulin, growth hormone, apomorphine, and PT-141.

14. The composition of claim 12, wherein said pharmaceutically active agent is insulin.

15. A method of transdermal delivery comprising administering to the skin of a subject in need thereof a therapeutically effective amount of a composition comprising a pharmaceutically acceptable carrier, a pharmaceutically active agent, and a peptide having an amino acid sequence as set forth in SEQ ID NO:1 (TD-2), SEQ ID NO:2 (TD-1), or SEQ ID NO:4 (TD-10).

* * * * *